(12) United States Patent
Salvemini

(10) Patent No.: US 9,132,131 B2
(45) Date of Patent: Sep. 15, 2015

(54) USE OF ADENOSINE A$_3$ RECEPTOR AGONISTS FOR TREATMENT OF NEUROPATHIC PAIN

(75) Inventor: Daniela Salvemini, Chesterfield, MO (US)

(73) Assignee: Saint Louis University, St. Louis, MO (US)

( * ) Notice: Subject to any disclaimer, the term of this patent is extended or adjusted under 35 U.S.C. 154(b) by 528 days.

(21) Appl. No.: 13/420,111

(22) Filed: Mar. 14, 2012

(65) Prior Publication Data

US 2012/0270829 A1 Oct. 25, 2012

Related U.S. Application Data

(60) Provisional application No. 61/477,964, filed on Apr. 21, 2011.

(51) Int. Cl.

| | |
|---|---|
| *A01N 43/04* | (2006.01) |
| *A01N 43/42* | (2006.01) |
| *A01N 37/12* | (2006.01) |
| *A01N 37/44* | (2006.01) |
| *A01N 33/02* | (2006.01) |
| *A61K 31/70* | (2006.01) |
| *A61K 31/44* | (2006.01) |
| *A61K 31/195* | (2006.01) |
| *A61K 31/135* | (2006.01) |
| *A61K 31/52* | (2006.01) |
| *A61K 31/7076* | (2006.01) |
| *A61K 45/06* | (2006.01) |

(52) U.S. Cl.
CPC ............. *A61K 31/52* (2013.01); *A61K 31/7076* (2013.01); *A61K 45/06* (2013.01)

(58) Field of Classification Search
CPC ... A61K 31/7076; A61K 31/52; A61K 45/05; A61K 2300/00
See application file for complete search history.

(56) References Cited

U.S. PATENT DOCUMENTS

| | | | |
|---|---|---|---|
| 6,004,945 | A | 12/1999 | Fukunaga |
| 2003/0139371 | A1 | 7/2003 | Gorny et al. |
| 2009/0181920 | A1 | 7/2009 | Watkins et al. |

OTHER PUBLICATIONS

Masakazu Hayashida et al., "Clinical application of adenosine and ATP for pain control" Journal of Anesthesia, Aug. 2005; pp. 225-235, vol. 19, No. 3.
Sawynok J., "Adenosine receptor activation and nociception" European Journal of Pharmacology 317, (1998), XP-002676053, pp. 1-11, vol. 346, No. 1., Department of Pharmacology, Dollhousie University, Halifax, NS, Canada B3H 4H7.
Borea P A et al., "A3 adenosine receptor: Pharmacology and role in disease" Handbook of Experimental Pharmacology, Springer-Verlag, Berlin, DE, vol. 193, Jan. 1, 2009, pp. 297-327, XP001539889, ISSN: 0171-2004 the whole document.
Joshi Bhalchandra V et al., "Purine derivatives as ligands for A(3) adenosine receptors" Current Topics in Medicinal Chemistry, Bentham Science Publishers Ltd., Netherlands, vol. 5, No. 3, Oct. 1, 2005, pp. 1275-1295, XP008089968, ISSN: 1568-0266, DOI:10. 2174/1568026057744463079 abstract table 1.
Devine S M et al., "Synthesis and evaluation of new N<6>-substituted adenosine-5'—N-methylcarboxamides as A3 adenosine receptor agonists" Bioorganic & Medicinal Chemistry, Pergamon, GB, vol. 18, No. 9, May 1, 2010, pp. 3078-3087, XP027030038, ISSN: 0968-0896 [retrieved on Apr. 26, 2010].
Balasubramanyan Sridhar et al., "Protective effect of adenosine in diabetic neuropathic pain is mediated through adenosine A1-receptors" Indian Journal of Physiology and Pharmacology, Association of Physiologists and Pharmacologists of India, IN, vol. 52, No. 3, Jul. 1, 2008, pp. 233-242, XP009146454, ISSN: 0019-5499 abstract.
Lavand'Homme P M et al., "Exogenous and endogenous adenosine enhance the spinal antiallodynic effects of morphine in a rat model of neuropathic pain" Pain Mar. 1999 LNKD-PUBMED:10204715, vol. 80, No. 1-2, Mar. 1999, pp. 31-36, XP002676048, ISSN: 0304-3959 abstract.
Borowicz K K et al., "N<6>-2-(4-Aminophenyl)ethyl-adenosine enhances the anticonvulsive action of conventional antiepileptic drugs in the kindling model of epilepsy in rats" European Neuropsychopharmacology, Elsevier Science Publishers, BV, Amsterdam, NL, vol. 10, No. 4, Jul. 1, 2000, pp. 237-243, XP027358350, ISSN: 0924-977X [retrieved on Jul. 1, 2000] abstract.
Segerdahl M et al., "The influence of adenosine, ketamine, and morphine on experimentally induced ishemic pain in healthy volunteers" Anesthesia and Analgesia Oct. 1994 LNKD-PUBMED:7943793, vol. 79, No. 4, Oct. 1994, pp. 787-791, XP002676049, ISSN: 0003-2999 abstract.
Doupeux L et al., "Measurement of the analgesic effects of remifentanil-adenosine combinations" Acta Anaesthesiologica Belgica 200703 BE, vol. 58, No. 1, Mar. 2007, p. 67, XP009159406, ISSN: 0001-5164 the whole document.
Inbar S et al., "Effects of adenosine in combination with calcium channel blockers in patients with primary pulmonary hypertension" Journal of the American College of Cardiology Feb. 1993 LNKD-PUBMED:8426006, vol. 21, No. 2, Feb. 1993, pp. 413-418, XP002676051, ISSN: 0735-1097 abstract.
Pareek S S et al., "Adenosine enhances analgesic effect of tricyclic antidepressants" Indian Journal of Pharmacology 1994 IN, vol. 26, No. 2, 1994, pp. 159-161, XP009159403, ISSN: 0253-7613 abstract.
Loram Lisa C et al., "Enduring reversal of neuropathic pain by a single intrathecal injection of adenosine 2A receptor agonists: a novel therapy for neuropathic pain" The Journal of Neuroscience: The Official Journal of the Society for Neuroscience Nov. 4, 2009 LNKD-PUBMED:19890011, vol. 29, No. 44, Nov. 4, 2009, pp. 14015-14025, XP002676052, ISSN: 1529-2401 abstract.

(Continued)

*Primary Examiner* — Lawrence E Crane
(74) *Attorney, Agent, or Firm* — Parker Highlander PLLC

(57) ABSTRACT

A method of treating neuropathic pain in a subject is provided. The method comprises administering to a subject a pharmaceutical composition comprising a therapeutically effective amount of an A$_3$AR agonist, optionally further including administering an analgesic.

20 Claims, 9 Drawing Sheets

(56) References Cited

OTHER PUBLICATIONS

Chen Zhoumou et al., "Controlling murine and rat chronic pain through A3 adenosine receptor activation" FASEB Journal: Official Publication of the Federation of American Societies for Experimental Biology May 2012 LNKD-PUBMED:22345405, vol. 26, No. 5, May 2012, pp. 1855-1865, XP009159205, ISSN:1530-6860 the whole document.

Hofer Michal et al., "Inhibition of cyclooxygenase-2 promotes the stimulatory action of adenosine A3 receptor agonist on hematopoiesis in sublethally [gamma] -irradiated mice" Biomedicine & Pharmacotherapy = Biomedecine & Pharmacotherapie Sep. 2011 LNKD-PUBMED:21719245, vol. 65, No. 6, Sep. 2011, pp. 427-431, XP002676054, ISSN: 1950-6007 abstract.

European Patent Office Search Report, (International Searching Authority), International Search Report and Written Opinion for PCT/US2012/029059; Date of Mailing: Jun. 6, 2012.

USE OF ADENOSINE A₃ RECEPTOR AGONISTS FOR TREATMENT OF NEUROPATHIC PAIN

CROSS REFERENCE TO RELATED APPLICATIONS

The Present Application claims the benefit of priority from U.S. Provisional Patent Application No. 61/477,964 entitled "USE OF ADENOSINE A3 RECEPTOR AGONISTS FOR TREATMENT OF NEUROPATHIC PAIN" and filed on 21 Apr. 2011, the contents of which are hereby incorporated by reference in their entirety to the extent permitted by law.

BACKGROUND

The $A_3$ adenosine receptor ($A_3AR$) belongs to the Gi-protein-associated cell membrane receptors. Activation of these receptors inhibits adenylate cyclase activity, inhibiting cAMP formation, leading to the inhibition of PKA expression and initiation of a number of downstream signaling pathways [1]. A variety of agonists to this receptor subtype have been synthesized, with IB-MECA ($N^6$-(3-iodobenzyl)-adenosine-5'-N-methyluronamide) and its chlorinated form CI-IB-MECA (2-chloro-$N^6$-(3-iodobenzyl)-adenosine-5'-N-methyluronamide), believed to be among the most potent and specific presently known $A_3AR$ agonists [2, 3]. Such compounds have shown efficacy in several animal models of inflammation, ischemia, reperfusion injuries, and cancer [1] and have advanced to clinical trial studies for rheumatoid arthritis and cancer.

Subjects with breast cancer, lung cancer, cervical cancer, ovarian cancer, germ cell tumors, acute leukemias and multiple myeloma who receive taxanes, platinum agents, vinca alkaloids and/or bortezomib as part of their initial therapy are at high risk of developing painful chemotherapy-induced peripheral neuropathy (CIPN) which can prematurely limit therapy and adversely impact quality of life. Thus, CIPN is a very serious complication of cancer chemotherapy and a major public health concern. It is estimated that the incidence of CIPN is as high as 70-90% in subjects receiving vincristine, cisplatin, oxaliplatin, and paclitaxel; 60% in subjects receiving docetaxel; 36-55% in subjects receiving bortezomib; and 40% in subjects receiving carboplatin [4, 5]. The development of CIPN with these agents appears not to be based on one single mechanism, as each of these drug classes possesses distinct anti-tumor mechanism of action [6]. There are currently no target-directed therapeutic approaches to treat CIPN. Consider the case of paclitaxel (Taxol®): Paclitaxel is a widely used chemotherapeutic agent indicated for the treatment of ovarian, breast, non-small cell lung carcinomas and Kaposi's sarcoma. Unfortunately, the dose-limiting side-effect of this highly efficacious antitumor drug is the precipitation of peripheral neuropathy accompanied by a chronic neuropathic pain syndrome that may resolve within weeks or months of drug termination, or it may last for years [7, 8]. The clinical management of these subjects is very difficult as current pain drugs are only marginally effective for treating the symptoms of CIPN, and they also display additional unacceptable side effects [9]. The tragedy here is that paclitaxel-evoked neuropathic pain is a leading cause of discontinuation of an otherwise successful therapy and paclitaxel doses are often restricted to levels that are suboptimal for killing tumor cells [7, 8]. The very same problem is seen in chemotherapeutics of other classes.

Chemotherapeutic strategies to treat various cancers are short-circuited by the numerous systemic side-effects observed. Pain, which is arguably the most debilitating and feared side-effect, greatly reduces the success of such strategies by limiting doses and imparting psychological distress. New methodologies to prevent or even reverse chemotherapy-induced chronic neuropathic pain would be transformative; indeed, the future development of a therapeutic of this nature is significant in two ways. First, the impact on quality of life for subjects would be enormous. The ability to reduce/eliminate CIPN amongst cancer survivors would result in lower costs related to the current chronic narcotic dependence needed to manage the pain. In addition, improved productivity in the work place would result, as many subjects with CIPN are unable to work and can no longer operate vehicles. Secondly, more lives may be saved. Subjects who currently would not be candidates for treatment (or continued treatment) with drugs such as paclitaxel due to the impending (or worsening) neuropathy, would instead benefit from full power anti-tumor dosages, if such dosages were to be made tolerable.

SUMMARY

Figure 1:
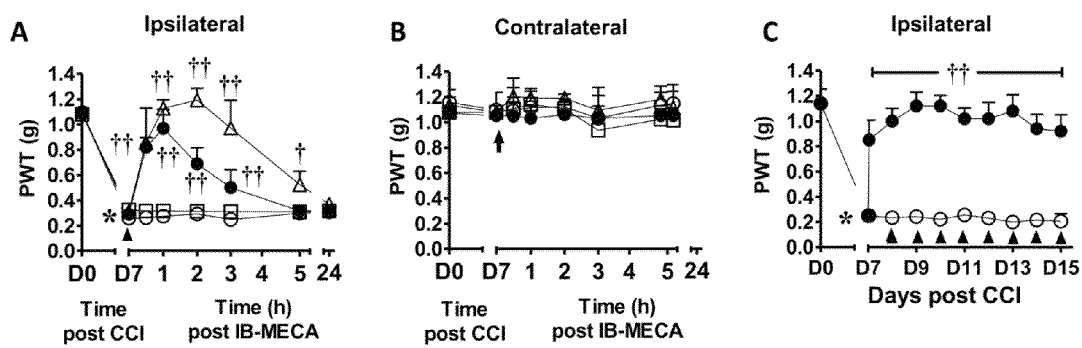
FIG. 1. $A_3AR$ agonists reverse mechano-allodynia in the CCI model. (A) IB-MECA (i.p.; 0.2, □; 0.5, ●; or 2 μmol/kg; Δ), but not its vehicle (○), on D7 after CCI (arrow) reversed mechano-allodynia in ipsilateral. (B) IB-MECA did not affect contralateral PWT (grams). (C) When compared to vehicle (○), daily i.p. injections (D8-D15, arrows) of IB-MECA (0.5 μmol/kg, ●) reversed mechano-allodynia to the same extent as D7. Results are expressed as mean±SD, n=5 mice, analyzed by ANOVA with Bonferroni comparisons. *$P<0.001$ (D7 or vehicle vs. D0); †$P<0.05$ or ††$P<0.001$ (IB-MECA at each time point post treatment vs. D7); °$P<0.001$ (agonist+antagonist vs. agonist alone).

In a first aspect, a method of treating neuropathic pain in a subject is provided. The method comprises administering to the subject a pharmaceutical composition comprising a therapeutically effective amount of an A$_3$AR agonist.

In a second aspect, a method of treating neuropathic pain in a subject is provided. The method comprises administering to the subject a first amount of an A$_3$AR agonist and a second amount of an analgesic, wherein the first and second amounts together comprise a therapeutically effective amount.

In a third aspect, a pharmaceutical composition for treating neuropathic pain is provided. The pharmaceutical composition comprises a first amount of an A$_3$AR agonist and a second amount of an analgesic, wherein the first and second amounts taken together comprise a pharmaceutically effective amount.

DEFINITIONS

As used in the specification and claims, the forms "a" and "an" include singular as well as plural references unless the context clearly dictates otherwise. For example, the term "an A$_3$AR agonist" can include one or more such agonists.

As used herein, the term "neuropathic pain" means a type of pain which is usually caused by damage to or dysfunction of the nervous system. Neuropathic pain may result from disorders of the peripheral nervous system or the central nervous system (brain and spinal cord). Thus, neuropathic pain may be divided into peripheral neuropathic pain, central neuropathic pain, or mixed (peripheral and central) neuropathic pain. Neuropathic pain may be the result of a number disease processes and may be due to damage in a number of locations. Central neuropathic pain is usually found in spinal cord injury, multiple sclerosis, and some strokes. Aside from diabetes and other metabolic conditions, the common causes of painful peripheral neuropathies include herpes zoster infection, HIV-related neuropathies, nutritional deficiencies, toxins, remote manifestations of malignancies, genetic, and immune mediated disorders or physical trauma to a nerve trunk. Neuropathic pain is common in cancer as a direct result of cancer on peripheral nerves (e.g., compression by a tumor), or as a side effect of chemotherapy, radiation injury or surgery.

"Treatment" as used herein includes the alleviation, prevention, reversal, amelioration or control of a pathology, disease, disorder, process, condition or event, including pain. In this context, the term "treatment" is further to be understood as embracing the use of a drug to inhibit, block, reverse, restrict or control progression of any type of pain.

As used herein, the term "chemotherapy" refers to the treatment of a disease by chemotherapeutic drugs. Example chemotherapeutic drugs include taxanes (e.g. paclitaxel), platinum-based agents (e.g. cisplatin, oxaliplatin, carboplatin), vinka alkaloids (e.g. vincristine), proteasome inhibitors (e.g. bortezomib), alkylating agents, antimetabolites, anthracyclines, plant alkaloids, topoisomerase inhibitors, and other antitumor agents. Other types of chemotherapy include the use of chemotherapeutic drugs in the treatment of autoimmune diseases such as multiple sclerosis, dermatomyositis, polymyositis, lupus, rheumatoid arthritis and the suppression of transplant rejections.

As used herein, the term "pharmaceutical composition" refers to compositions of matter comprising at least one pharmaceutical compound.

As used herein, the term "pharmaceutical compound" or "drug" refers to a free compound, its therapeutically suitable salts, solvates such as hydrates, specific crystal forms of the compound or its salts, or therapeutically suitable prodrugs of the compound.

The term "therapeutically suitable salt," refers to salts or zwitterions of pharmaceutical compounds which are water or oil-soluble or dispersible, suitable for treatment of disorders and effective for their intended use. The salts may be prepared, for instance, during the final isolation and purification of the compounds or separately by reacting an amino group of the compounds with a suitable acid. For example, a compound may be dissolved in a suitable solvent, such as but not limited to methanol and water, and treated with at least one equivalent of an acid, for instance hydrochloric acid. The resulting salt may precipitate out and be isolated by filtration and dried under reduced pressure. Alternatively, the solvent and excess acid may be removed under reduced pressure to provide the salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric, and the like. The amino groups of a compound may also be quaternized with alkyl chlorides, bromides, and iodides such as methyl, ethyl, propyl, isopropyl, butyl, lauryl, myristyl, stearyl, and the like.

Basic addition salts may be prepared, for instance, during the final isolation and purification of pharmaceutical compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts may derived, for example, from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like.

The term "therapeutically suitable prodrug," refers to those prodrugs or zwitterions which are suitable for use in contact with the tissues of subjects and are effective for their intended use. The term "prodrug" refers to compounds that are transformed in vivo to a pharmaceutical compound, for example, by hydrolysis in blood. The term "prodrug," refers to compounds that contain, but are not limited to, substituents known as "therapeutically suitable esters." The term "therapeutically suitable ester," refers to alkoxycarbonyl groups appended to the parent molecule on an available carbon atom. More specifically, a "therapeutically suitable ester," refers to alkoxycarbonyl groups appended to the parent molecule on one or more available aryl, cycloalkyl and/or heterocycle groups. Compounds containing therapeutically suitable esters are an example, but are not intended to limit the scope of compounds considered to be prodrugs. Examples of prodrug ester groups include pivaloyloxymethyl, acetoxymethyl, phthalidyl, indanyl and methoxymethyl, as well as other such groups known in the art. Other examples of prodrug ester groups are found in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The terms "pharmaceutically effective amount" and "effective amount", as used herein, refer to an amount of a pharmaceutical formulation that will elicit the desired therapeutic effect or response when administered in accordance with the desired treatment regimen.

DETAILED DESCRIPTION

The present disclosure is based on the discovery that $A_3AR$ agonists can be used as pharmaceutical compounds in treatments against pain. In particular, $A_3AR$ agonists have been found to be effective in the treatment of neuropathic pain, especially with regard to blocking and/or reversing the development of chemotherapy-induced neuropathic pain (CIPN) and nerve-injury-derived neuropathic pain. Thus, $A_3AR$ agonists may be used in shielding cancer patients from the pain due to chemotherapeutic agents and other causes. Moreover, $A_3AR$ agonists and analgesics have been found to exhibit a synergistic effect in the treatment of neuropathic pain.

Thus, in a first aspect, a method of treating neuropathic pain is provided. The method comprises administering to a subject a pharmaceutical composition comprising a therapeutically effective amount of an $A_3AR$ agonist. Various types of compounds having an $A_3AR$ agonist activity are known, but no report in the past has discussed an analgesic effect of such a compound or a combination of such compounds in a neuropathic pain model. Without being bound to any particular theory, it is believed that the $A_3AR$ is highly expressed in pathological cells; $A_3AR$ agonists are therefore believed to tend to bind exclusively to the pathological cells, thereby inducing a specific therapeutic effect.

It can be confirmed that a compound has an $A_3AR$ activity by known methods [76-84]. Examples of $A_3AR$ agonists that may be used in the treatment of neuropathic pain include, but are not limited to, $N^6$-benzyladenosine-5'-N-methyluronamides such as $N^6$-(3-iodobenzyl)-adenosine-5'-N-methyluronamide, also known as IB-MECA [17], and 2-Chloro-$N^6$-(3-iodobenzyl)-adenosine-5'-N-methyluronamide (also known as 2-CI-IB-MECA; (N)-methanocarba nucleosides such as (1R,2R,3S,4R)-4-(2-chloro-6-((3-chlorobenzyl)amino)-9H-purin-9-yl)-2,3-dihydroxy-N-methylbicyclo[3.1.0]hexane-1-carboxamide (also known as CF502, Can-Fite Biopharma, MA); (2S,3S,4R,5R)-3-amino-5-[6-(2,5-dichlorobenzylamino)purin-9-yl]-4-hydroxytetrahydrofuran-2-carboxylic acid methylamide (also known as CP-532,903); (1'S,2'R,3'S,4'R,5'S)-4-(2-chloro-6-(3-chlorobenzylamino)-9H-purin-9-yl)-2,3-dihydroxy-N-methylbicyclo[3.1.0]hexane-1-carboxamide (also known as MRS-3558), 2-(1-Hexynyl)-N-methyladenosine; (1S,2R,3S,4R)-2,3-dihydroxy-4-(6-((3-iodobenzyl)amino)-4H-purin-9(5H)-yl)-N-methylcyclopentanecarboxamide (also known as CF101, Can-Fite), (1S,2R,3S,4R)-4-(2- chloro-6-((3-iodobenzyl)amino)-4H-purin-9(5H)-yl)-2,3-dihydroxy-N-methylcyclopentanecarboxamide (also known as CF102, Can-Fite); (1'R,2'R,3'S,4'R,5'S)-4-{2-chloro-6-[(3-iodophenylmethyl)amino]purin-9-yl}-1-(methylaminocarbonyl)-bicyclo[3.1.0]hexane-2,3-diol (also known as MRS1898); and 2-Dialkynyl derivatives of (N)-methanocarba nucleosides [82]. Preferred compounds include, but are not limited to, IB-MECA, CF101, and CF102.

Also included are $A_3AR$ allosteric modulators which enhance the receptor activity in the presence of the native ligand [18], such as 2-cyclohexyl-N-(3,4-dichlorophenyl)-1H-imidazo[4,5-c]quinolin-4-amine (also known as CF602, Can-Fite). However, the above-listed $A_3AR$ agonists are by no means exclusive and other such agonists may also be used. The administration of $A_3AR$ agonists covalently bound to polymers is also contemplated. For example, $A_3AR$ agonists may be administered in the form of conjugates where an agonist is bound to a polyamidoamine (PAMAM) dendrimer [83, 84].

The administration of a pharmaceutical composition comprising an $A_3AR$ agonist has been found to alleviate the symptoms of neuropathic pain regardless of the cause of the pain or location of the bodily pain, and treats pain of varying severity, e.g. mild, moderate and severe pain in acute and/or chronic modes. Example causes of neuropathic pain include, but are not limited to, spinal cord injury, multiple sclerosis, stroke, diabetes, herpes zoster infection, HIV-related neuropathies, nutritional deficiencies, toxins, remote manifestations of malignancies, genetic, immune mediated disorders or physical trauma to a nerve trunk, cancer, chemotherapy, radiation injury or surgery.

It is contemplated that the administration of an $A_3AR$ agonist will be especially suited to the treatment of CIPN induced by a chemotherapeutic drug. Example types of chemotherapeutic drugs include podophyllotoxins, taxanes, platinum complexes, vinca alkaloids, proteasome inhibitors, colchicines, eribulin, lenolidamide, ixabepilone, interpherons, thalidomide, etoposide, ifosfamide, procarbazine, cytarabine, gemcitabine, and arsenic. Example chemotherapeutic drugs include, but are not limited to, one or more of the following: anti-cancer alkylating or intercalating agents (e.g., Mechlorethamine, Chlorambucil, Cyclophosphamide, Melphalan, and Ifosfamide); antimetabolites (e.g., Methotrexate); purine antagonists and pyrimidine antagonists (e.g., 6-Mercaptopurine, 5-Fluorouracil, Cytarablle, Capecitabine and Gemcitabine); spindle poisons (e.g., Vinblastine, Vincristine, Vinorelbine and Paclitaxel); podophyllotoxins (e.g., Etoposide, Irinotecan, Topotecan); antibiotics (e.g., Doxorubicin, Bleomycin and Mitomycin); nitrosoureas (e.g., Carmustine, Lomustine); inorganic ions (e.g., Cisplatin, Carboplatin, Oxaliplatin or Oxiplatin); enzymes (e.g., Asparaginase); hormones (e.g., Tamoxifen, Leuprolide, Flutamide and Megestrol); proteasome inhibitors (such as Velcade); other kinase inhibitors (e.g., inhibitors of Src, BRC/Abl, kdr, flt3, aurora-2, glycogen synthase kinase 3 ("GSK-3"), EGF-R kinase (e.g., Iressa, Tarceva, VEGF-R kinase, PDGF-R kinase); antibodies, soluble receptor or other receptor antagonists against a receptor or hormone implicated in a cancer (including receptors such as EGFR, ErbB2, VEGFR, PDGFR, and IGF-R); and agents such as Herceptin (or other anti-Her2 antibodies), Avastin, and Erbitux. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

$A_3AR$ agonists may also be used to treat pain associated with CIPN induced by one or more combinations comprising a chemotherapeutic drug as part of a treatment regimen. Example combinations include, but are not limited to: CHOPP (cyclophosphamide, doxorubicin, vincristine, prednisone, and procarbazine); CHOP (cyclophosphamide, doxorubicin, vincristine, and prednisone); COP (cyclophosphamide, vincristine, and prednisone); CAP-BOP (cyclophosphamide, doxorubicin, procarbazine, bleomycin, vincristine, and prednisone); m-BACOD (methotrexate, bleomycin, doxorubicin, cyclophosphamide, vincristine, dexamethasone, and leucovorin); ProMACE-MOPP (prednisone, methotrexate, doxorubicin, cyclophosphamide, etoposide, leucovorin, mechloethamine, vincristine, prednisone, and procarbazine); ProMACE-CytaBOM (prednisone, methotrexate, doxorubicin, cyclophosphamide, etoposide, leucovorin, cytarabine, bleomycin, and vincristine); MACOP-B (methotrexate, doxorubicin, cyclophosphamide, vincristine, prednisone, bleomycin, and leucovorin); MOPP (mechloethamine, vincristine, prednisone, and procarbazine); ABVD (adriamycin/doxorubicin, bleomycin, vinblastine, and dacarbazine); MOPP (mechloethamine, vincristine, prednisone and procarbazine) alternating with ABV (adriamycin/doxorubicin, bleomycin, and vinblastine); MOPP (mechloethamine, vincristine, prednisone, and procarbazine) alternating with ABVD (adriamycin/doxorubicin, bleomycin, vinblastine, and dacarbazine); ChIVPP (chlorambucil, vinblastine, procarbazine, and prednisone); IMVP-16 (ifosfamide, methotrexate, and etoposide); MIME (methyl-gag, ifosfamide, methotrexate, and etoposide); DHAP (dexamethasone, high-dose cytaribine, and cisplatin); ESHAP (etoposide, methylpredisolone, high-dose cytarabine, and cisplatin); CEPP(B) (cyclophosphamide, etoposide, procarbazine, prednisone, and bleomycin); CAMP (lomustine, mitoxantrone, cytarabine, and prednisone); CVP-1 (cyclophosphamide, vincristine, and prednisone), ESHOP (etoposide, methylpredisolone, high-dose cytarabine, vincristine and cisplatin); EPOCH (etoposide, vincristine, and doxorubicin for 96 hours with bolus doses of cyclophosphamide and oral prednisone), ICE (ifosfamide, cyclophosphamide, and etoposide), CEPP(B) (cyclophosphamide, etoposide, procarbazine, prednisone, and bleomycin), CHOP-B (cyclophosphamide, doxorubicin, vincristine, prednisone, and bleomycin), CEPP-B (cyclophosphamide, etoposide, procarbazine, and bleomycin), and P/DOCE (epirubicin or doxorubicin, vincristine, cyclophosphamide, and prednisone).

For use in accordance with this first aspect, the appropriate dosage is expected to vary depending on, for example, the particular $A_3AR$ agonist employed, the mode of administration, and the nature and severity of the condition to be treated as well as the specific condition to be treated and is within the purview of the treating physician. Usually, an indicated administration dose may be in the range between about 0.1 to about 1000 µg/kg body weight. In some cases, the administration dose of the $A_3AR$ agonist may be less than 400 µg/kg body weight. In other cases, the administration dose may be less than 200 µg/kg body weight. In yet other cases, the administration dose may be in the range between about 0.1 to about 100 µg/kg body weight. The dose may be conveniently administered once daily, or in divided doses up to, for example, four times a day or in sustained release form.

$A_3AR$ agonists may be administered by any conventional route, in particular: enterally, topically, orally, nasally, e.g. in the form of tablets or capsules, via suppositories, or parenterally, e.g. in the form of injectable solutions or suspensions, for intravenous, intra-muscular, sub-cutaneous, or intra-peritoneal injection.

Suitable formulations and pharmaceutical compositions of $A_3AR$ agonists will include those formulated in a conventional manner using one or more physiologically acceptable carriers or excipients, and any of those known and commercially available and currently employed in the clinical setting. Thus, the compounds may be formulated for oral, buccal, topical, parenteral, rectal or transdermal administration or in a form suitable for administration by inhalation or insufflation (either orally or nasally).

For oral administration, pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). Tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). Preparations may also contain buffer salts, flavoring, coloring and sweetening agents as appropriate.

Preparations for oral administration may also be suitably formulated to give controlled-release or sustained release of the active compound(s) over an extended period. For buccal administration the compositions may take the form of tablets or lozenges formulated in a conventional manner known to the skilled artisan.

$A_3AR$ agonists may also be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain additives such as suspending, stabilizing and/or dispersing agents. Alternatively, the $A_3AR$ agonists may be in powder form for constitution with a suitable vehicle, e.g. sterile pyrogen-free water, before use. $A_3AR$ agonists may also be formulated for rectal administration as suppositories or retention enemas, e.g. containing conventional suppository bases such as cocoa butter or other glycerides.

In a second aspect, a method of treating neuropathic pain in a subject, comprising administering to the subject an $A_3AR$ agonist in conjunction with an analgesic, is provided. This second aspect is based on the discovery that $A_3AR$ agonists and analgesics exhibit a synergistic effect increasing the potency of the analgesics. In other words, the administration of these compounds exhibits synergistic effects that exceed the mere additive contribution of the individual components. As a result, synergistically effective amounts of $A_3AR$ agonist and analgesic taken together may be less than the effective amount of the $A_3AR$ agonist or analgesic administered as monotherapies.

The method may involve administering to a subject a first amount of an $A_3AR$ agonist in combination with a second amount of analgesic, wherein the first and second amount together comprise a pharmaceutically effective amount. Because of the above synergistic effect, the first amount, the second amount, or both may be less than effective amounts of each compound administered as monotherapies. Therapeutically effective amounts of the $A_3AR$ and analgesic are co-administered to the subject, i.e., are administered to the subject simultaneously or separately, in any given order and by the same or different routes of administration. It may be advantageous to initiate administration of the $A_3AR$ agonist first, for example one or more days or weeks prior to initiation of administration of the analgesic. Moreover, additional drugs may be given in conjunction with the above combination therapy.

The method of this second aspect may be used to alleviate the symptoms of neuropathic pain regardless of the cause of the pain, for example, but not limited to, spinal cord injury, multiple sclerosis, stroke, diabetes, herpes zoster infection, HIV-related neuropathies, nutritional deficiencies, toxins, remote manifestations of malignancies, genetic, immune mediated disorders or physical trauma to a nerve trunk, cancer, chemotherapy, radiation injury or surgery.

Examples of $A_3AR$ agonists that may be used in conjunction with an analgesic include, but are not limited to, $N^6$-benzyladenosine-5'-N-methyluronamides such as IB-MECA and 2-CI-IB-MECA; (N)-methanocarba nucleosides such as CF502; CP-532,903; MRS-3558; CF101; CF102; MRS1898, and 2-Dialkynyl derivatives of (N)-methanocarba nucleosides. Preferred compounds include, but are not limited to, IB-MECA, CF101, and CF102. Also included are $A_3AR$ allosteric modulators which enhance the receptor activity in the presence of the native ligand, such as CF602. However, the above-listed $A_3AR$ agonists are by no means exclusive and other such agonists may also be used. The administration of $A_3AR$ agonists covalently bound to polymers is also contemplated. For example, $A_3AR$ agonists may be administered in the form of conjugates where an agonist is bound to a polyamidoamine (PAMAM) dendrimer.

The analgesic administered in conjunction with an $A_3AR$ agonist may be selected in relation to the particular condition being treated, and preferably has proven efficacy in the treatment of pain without significant potential for addiction. Currently known analgesics include, but are not limited to, opioids, morphinomimetics, antidepressants, antiepileptics, NMDA receptor antagonists, fatty acid amine hydrolyase inhibitors, anticonvulsives, non-steroidal anti-inflammatory drugs (NSAIDs), COX-2 inhibitors, NOS inhibitors, and calcium channel subunit $\alpha_2\delta$ ligands.

Example opioids include any natural or synthetic opioid analgesic, such as morphine, fentanyl, codeine, thebaine, diacetylmorphine (heroin), dihydrocodeine, hydrocodone, hydromorphone, nicomorphine, oxycodone, oxymorphone, alphamethylfentanyl, alfentanil, sufentanil, remifentanil, carfentanyl, ohmefentanyl, nocaine, pethidine (meperidine), ketobemidone, MPPP, allylprodine, prodine, PEPAP, propoxyphene, dextropropoxyphene, dextromoramide, bezitramide, piritramide, methadone, dipipanone, levoalphacetylmethadol (LAAM), loperamide, diphenoxylate, pentazocine, phenazocine, buprenorphine, etorphine, butorphanol, nalbuphine, levorphanol, levomethorphan, dezocine, lefetamine, tilidine, tramadol, propoxyphene, and oxycodone. As intended herein, an opioid also encompasses any natural or synthetic narcotic antagonist such as nalmefene, naloxone or naltrexone as well as any natural or synthetic mixed opioid agonist/antagonist such as nalbuphine, butorphanol, buprenorphine and pentazocine.

Example non-steroidal anti-inflammatory drugs (NSAIDs) include aspirine, ibuprofen, acetaminophen, naproxen, fenoprofen, ketoprofen, flurbiprofen, oxaprozin, indomethacin, sulindac, etodolac, ketorolac, diclofenac, nabumetone, piroxicam, meloxicam, tenoxicam, droxicam, lornoxicam, isoxicam, mefenamic acid, meclofenamic acid, flufenamic acid, tolfenamic acid, celecoxib, rofecoxib, valdecoxib, parecoxib, lumiracoxib, etoricoxib, firocoxib, nimesulide, and licofelone. Example antidepressants include tricyclic antidepressants such as: amitriptyline, amitriptylinoxide, butriptyline, clomipramine, demexiptiline, desipramine, dibenzepin, dimetacrine, dosulepin, doxepin, imipramine, imipraminoxide, lofepramine, melitracen, metapramine, nitroxazepine, nortriptyline, noxiptiline, pipofezine, propizepine, protriptyline, and quinupramine; amineptine, norepinephrine, iprindole, opipramol, tianeptine, trimipramine, carbamezapine, and flupirtine.

It is contemplated that $A_3AR$ agonists will be especially suited to the treatment of pain when co-administered with an opioid, a tricyclic antidepressant, or an analgesic believed to bind the calcium channel subunit $\alpha_2\delta$, i.e. a calcium channel subunit $\alpha_2\delta$ ligand. Examples of such ligands include GABA analogs, such as gabapentin (2-[1-(aminomethyl)cyclohexyl] acetic acid) and pregabalin ((S)-3-(aminomethyl)-5-methylhexanoic acid).

The relative amounts of the compounds may be selected to provide for synergistic pain relief. For example, a suitable ratio of IB-MECA to gabapentin may be in the range of from about 0.1 part by weight of the IB-MECA to from about 3 to about 30 parts by weight of the gabapentin. A suitable ratio of IB-MECA to morphine may be in the range of from about 0.1 part by weight of the IB-MECA to from about 1 to about 5 parts by weight of the morphine. While these ratios are calculated with respect to the free compounds (non-salt forms), it should be understood that the equivalent ratios can also readily be determined for pharmaceutically acceptable salts or prodrugs of the compounds by using a ratio of the molecular weights of the salts.

In some cases, co-administration of the $A_3AR$ agonist and analgesic is achieved by formulating the compounds together in a combination composition. Accordingly, in a third aspect, a combination composition for treating neuropathic pain is provided.

Examples of $A_3AR$ agonists that may be used in a combination composition together with an analgesic include, but are not limited to, $N^6$-benzyladenosine-5'-N-methyluronamides such as IB-MECA and 2-CI-IB-MECA; (N)-methanocarba nucleosides such as CF502; CP-532,903; MRS-3558; CF101; CF102; MRS1898, and 2-Dialkynyl derivatives of (N)-methanocarba nucleosides. Preferred compounds include, but are not limited to, IB-MECA, CF101, and CF102. Also included are $A_3AR$ allosteric modulators which enhance the receptor activity in the presence of the native ligand, such as CF602. However, the above-listed $A_3AR$ agonists are by no means exclusive and other such agonists may also be used. The administration of $A_3AR$ agonists covalently bound to polymers is also contemplated. For example, $A_3AR$ agonists may be administered in the form of conjugates where an agonist is bound to a polyamidoamine (PAMAM) dendrimer.

The analgesic administered in the combination composition may be selected in relation to the particular condition being treated, and preferably has proven efficacy in the treatment of pain without significant potential for addiction. Currently known analgesics include, but are not limited to, opioids, morphinomimetics, antidepressants, antiepileptics, NMDA receptor antagonists, fatty acid amine hydrolyase inhibitors, anticonvulsives, non-steroidal anti-inflammatory drugs (NSAIDs), COX-2 inhibitors, NOS inhibitors, and calcium channel subunit $\alpha_2\delta$ ligands.

In some cases, the combination composition comprises a first pharmaceutically acceptable composition containing a first amount of an $A_3AR$ agonist, and a second pharmaceutically acceptable composition comprising a second amount of an analgesic, wherein the first and second amounts taken together comprise a pharmaceutically effective amount. The first amount, the second amount, or both may be less than effective amounts of each compound administered as monotherapies.

In other cases, the combination composition is a pharmaceutically acceptable composition comprising a first amount of an $A_3AR$ agonist and a second amount of an analgesic, wherein the first and second amounts taken together comprise a pharmaceutically effective amount. The first amount, the second amount, or both may be less than effective amounts of each compound administered as monotherapies.

Suitable combination compositions will include those formulated in a conventional manner using one or more physiologically acceptable carriers or excipients, and any of those known and commercially available and currently employed in the clinical setting. Thus, the compounds of a combination composition may be formulated for oral, buccal, topical, parenteral, rectal or transdermal administration or in a form suitable for administration by inhalation or insufflation (either orally or nasally).

For oral administration, combination compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). Tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). Preparations may also contain buffer salts, flavoring, coloring and sweetening agents as appropriate.

Preparations for oral administration may also be suitably formulated to give controlled-release or sustained release of the active compound(s) over an extended period. For buccal administration the compositions may take the form of tablets or lozenges formulated in a conventional manner known to the skilled artisan.

Combination compositions may also be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain additives such as suspending, stabilizing and/or dispersing agents. Alternatively, the active ingredients may be in powder form for constitution with a suitable vehicle, e.g. sterile pyrogen-free water, before use.

The combination compositions for use according to this aspect may also be formulated for rectal administration as suppositories or retention enemas, e.g. containing conventional suppository bases such as cocoa butter or other glycerides.

While formulation of the $A_3AR$ agonist and analgesic has been described with regards to the combination of the compounds into a combination composition, it should also be understood that the compounds may be co-administered in separate preparations, such as a first unit dosage form comprising an $A_3AR$ agonist, and a second unit dosage form suitable for co-administration with the first unit dosage form comprising an analgesic. Other methods or modes of co-administration not specifically described herein should also be understood to be encompassed.

The invention has been described with reference to various illustrative embodiments and techniques. However, it should be understood that many variations and modifications, as are known in the art, may be made while remaining within the scope of the claims of the present application. The examples that follow are illustrative and are not intended to be limiting.

EXAMPLES

Materials and Methods

Materials: IB-MECA, CI-IB-MECA, DPCPX (8-cyclopentyl-1,3-dipropylxanthine) and SCH-442416 [2-(2-furanyl)-7-[3-(4-methoxyphenyl)propyl]-7Hpyrazolo[4,3-e][1,2,4]triazolo[1,5-C]pyrimidin-5-amine] were purchased from Tocris (Ellisville, Mo., USA). MRS1898 ((1'R,2'R,3'S,4'R,5'S)-4-{2-chloro-6-[(3-iodophenylmethyl)amino]purin-9-yl}-1-(methylaminocarbonyl)-bicyclo[3.1.0]hexane-2,3-diol) was synthesized as described previously [45, 46]. Morphine was a kind gift from Mallinckrodt (St. Louis, Mo., USA). Paclitaxel, oxaliplatin and bortezomib were purchased commercially and respectively from Parenta Pharma (Yardley, Pa., USA), Oncology Supply (Dothan, Ala., USA) and Selleck Chemicals (Houston, Tex., USA). For cell culture: the media was purchased from Mediatech (Dulbecco's Minimal Essential Media and McCoy's 5A; Manassas, Va., USA) or Sigma-Aldrich (L12; St. Louis, Mo., USA); fetal bovine serum from Thermo Scientific Hyclone (Waltham, Mass., USA); and the penicillin/streptomycin from Invitrogen (Carlsbad, Calif., USA). Cell lines were kind gifts from colleagues: SKBR3 (Dr. Joseph Baldassare, Saint Louis University), SW480 (Stephanie Knebel, Saint Louis University), and RPMI 8226 (Jaki Kornbluth, Saint Louis University). MRS1523 (3-propyl-6-ethyl-5[(ethylthio)carbonyl]-2-phenyl-4-propyl-3-pyridine-carboxylate), gabapentin, amitriptyline, and all other chemicals were purchased from Sigma-Aldrich (St. Louis, Mo., USA).

Experimental animals. Male Sprague Dawley rats (200-220 g) or mice (25-30 g) from Harlan (Indianapolis, Ind., USA) were housed 3-4 (for rats) and 5 (for mice) per cage in a controlled environment (12 hours light/dark cycles) with food and water available ad libitum. Experiments were performed in accordance with International Association for the Study of Pain, NIH guidelines on laboratory animal welfare and Saint Louis University Institutional Animal Care and Use Committee recommendations. Experimenters were blinded to treatment conditions in all experiments.

CCI model of neuropathic pain. CCI to the sciatic nerve of the left hind leg in mice was performed under general anaesthesia using the well-characterized Bennett model [47]. Briefly, mice (weighing 25-30 g at the time of surgery) were anesthetized with 3% isoflurane/100% $O_2$ inhalation and maintained on 2% isoflurane/100% $O_2$ for the duration of surgery. The left thigh was shaved, scrubbed with Nolvasan® and a small incision (1-1.5 cm in length) was made in the middle of the lateral aspect of the left thigh to expose the sciatic nerve. The nerve was loosely ligated around the entire diameter of the nerve at three distinct sites (spaced 1 mm apart) using silk sutures (6.0). The surgical site was closed with a single muscle suture and a skin clip. Pilot studies established that under our experimental conditions peak mechano-allodynia develops by day 5-day 7 (D5-D7) following CCI. Test substances or their vehicles were given subcutaneously (s.c.), intraperitoneally (i.p.) or orally by gavage (0.1 ml) at peak mechano-allodynia (D7).

Induction of chemotherapy-induced neuropathic pain in rats: Paclitaxel or vehicle (Cremophor EL and 95% anhydrous ethanol in 1:1 ratio) were injected i.p. on four alternate days (2 mg/kg on D0, 2, 4 and 6 with a final cumulative dose of 8 mg/kg) [48]. Oxaliplatin or vehicle (5% dextrose) was injected i.p. in rats on five consecutive days (D0-D4) for a final cumulative dose of 10 mg/kg (31). Bortezomib or vehicle (5% Tween 80, 5% ethanol) was injected i.p. in rats on five consecutive days (D0-D4; 0.2 mg/kg) for a final cumulative dose of 1 mg/kg (G. J. Bennett and W. H. Xiao, personal communication). Test substances or their vehicle were given i.p. (0.2 ml) 30 min before the chemotherapeutic agent or its vehicle on D0 (baseline) and then daily until D15 or D17. Behavioral responses (mechano-allodynia and mechano-hyperalgesia) were measured on D0 prior to the first i.p. injection of the chemotherapeutic agent and subsequently at various time points. If testing coincided with a day when rats received test substance, behavioral measurements were taken always before the injection of the test substance. Chemotherapeutic treatments result in bilateral allodynia and hyperalgesia without differences in left and right paw withdrawal threshold (PWT, grams) in any group at any time point, thus values from both paws were averaged. None of the animals exhibited signs of observable toxicities; they exhibited normal posture, grooming, locomotor behavior, hair coat was normal without signs of piloerection or porphyrin, and body weight gain was normal and comparable to vehicle-treated rats.

Behavioral testing. Mechano-allodynia was measured in CCI and paclitaxel studies after first acclimating the animals to elevated cages with a wire mesh floor for 15 minutes. The plantar aspect of hindpaws were probed three times with calibrated von Frey filaments (Stoelting, mice: 0.07-2.00 grams; rats: 0.407-26 grams) according to the "up-and-down" method [50]. In oxaliplatin or bortezomib studies, allodynia was assessed with an electronic version of the VF test (dynamic plantar aesthesiometer, model 37450; Ugo Basile, Milan, Italy). Briefly, each rat was placed in a Plexiglas chamber (28×40×35-cm, wire mesh floor) and after its acclimation, a servo-controlled mechanical stimulus was applied to the plantar surface that exerted a progressively increasing punctate pressure up to 50 grams within 10 seconds. Mechanical threshold was assessed three times at each time point to yield a mean value, reported as PWT (grams). The development of mechano-allodynia is evidenced by a significant ($P<0.05$) reduction in mechanical mean PWT (grams) at forces that failed to elicit withdrawal responses on D0 before CCI or chemotherapeutic/vehicle treatment. Mechano-hyperalgesia was assessed in rats by the Randall and Sellitto paw pressure test [51] using an analgesiometer (Ugo Basile). The nociceptive threshold was defined as the force (grams) at which the rat withdrew its paw (cut off set at 250 grams).

Tail flick and hot plate assay in mice for acute nociception. The tail flick test, which measures latency(s) of tail withdrawal from a noxious radiant heat source (Ugo Basile; model number 37360) was used to measure thermal nociceptive sensitivity in mice with baseline latencies of 3-5 seconds and a cut-off time of 15 seconds to prevent tissue injury [52]. Tail flick latencies were taken before and at 30, 60 and 120 minutes after i.p. injection of IB-MECA, MRS1898 (0.5 μmol/kg) or its vehicle (0.1% DMSO in saline). For the hot plate test, nociceptive thresholds were determined as previously reported by our group by measuring latencies (in seconds) of mice placed in a transparent glass cylinder on a hot plate maintained at 52° C. [53, 54]. Responses indicative of nociception included intermittent lifting and/or licking of the hindpaws or escape behavior. Hot plate latencies were taken in mice from all groups before and after drug administration. A cut-off latency of 15 seconds was employed to prevent tissue damage.

Rotarod test in mice: Mice were trained before experimentation for their ability to remain for 60 seconds on a revolving Rotarod for mice apparatus (Ugo Basile; accelerating units increasing from 5 to 40 rpm in 60 sec). Mice were injected i.p. with IB-MECA, MRS1898 (0.5 μmol/kg) or vehicle (0.1% DMSO in saline) and then examined at 30, 60 and 120 minutes after administration for motor impairments on the Rotarod. The latency time to fall off the Rotarod was determined with a cut-off time of 120 seconds.

Effects of IB-MECA on antitumor activity of paclitaxel, oxaliplatin and bortezomib. Cells were cultured and assayed in DMEM (SKBR3; human breast cancer cells [55]), L15 (SW480; human colon cancer cells [56]) or RPMI 1620 (RPMI 8226; human multiple myeloma cells [57]) supplemented with heat-denatured 10% FBS and penicillin/streptomycin at 37° C., 0% (SW480) or 5% $CO_2$ (SKBR3 and RPMI 8226), 95% humidity. The antitumor activities of these agents were measured in cells (6.25×104 cells/well) cultured overnight in 24-well plates (SKBR3 and SW480; BD Biosciences) or 12 mm×7.5 mm culture tubes (RPMI 8226; BD Biosciences) in complete media. This plating regiment yielded 60% confluent plate cultures for testing. After equilibrating in fresh media (5 hours), cells were treated for 48 hours with IB-MECA (10 nM) or its vehicle (PBS) and paclitaxel (1-100 nM) or its vehicle (1% Cremophor EL: 0.9% ethanol); oxaliplatin (1-100 μM) or its vehicle (0.01% DMSO in PBS); or bortezomib (1-100 nM) or its vehicle (0.05% dextrose). Two naïve control wells were included as a control for 100% survival. Cell survival was determined using a MTT (3-(4,5-dimethylthiazol-2-yl)-2,5-diphenyltetrazolium bromide) assay adapted from a previously described assay [58, 59]. Cells were incubated with MTT (500 μg/ml) for 75 minutes at 37° C., 0% or 5% $CO_2$, 95% humidity, removing the media and dissolving the tetrazolium crystals in isopropanol. The tetrazolium absorption ($A_{560-570\ nm}$) was measured from paclitaxel experiments using a Unicam UV1 spectrophotometer (ThermoFisher Scientific, Waltham, Mass.) and from oxaliplatin or bortezomib experiments using a Glomax® Multi-Detection system (Promega, Madison, Wis.). The antitumor effects of IB-MECA alone were determined as % Survivability=($A_{560-570\ nm}$ of chemotherapeutic vehicle+IB-MECA)/(mean $A_{560-570\ nm}$ of the naïve control wells)×100. The $LD_{50}$ of each chemotherapeutic agent+IB-MECA or its vehicle was calculated using three-parameter non-linear analysis using % Survivability=($A_{560-570\ nm}$ of chemotherapeutic+IB-MECA or its vehicle)/(mean $A_{560-570\ nm}$ chemotherapeutic vehicle+vehicle of IB-MECA)×100. The top and bottom plateaus were constrained using GraphPad Prism v5.03 (GraphPad Software, Inc.).

Determining $ED_{50}$ values. Dose response data were curve-fitted using the least sum of square method by a normalized 4-parameter, variable slope non-linear analysis of the % Reversal of Mechano-allodynia in CCI and % Prevention of Mechano-allodynia or Mechano-hyperalgesia in CIPN using GraphPad Prism (Release 5.03, GraphPad Software, Inc.) from which the $ED_{50}$ was determined and reported with the 95% confidence interval (95% CI). In the CCI model, the % Reversal of Mechano-allodynia=($PWT_{1h}-PWT_{D7}$)/($PWT_{D0}-PWT_{D7}$)×100, where $PWT_{D0}$=Paw Withdrawal Threshold (g) at D0, $PWT_{1h}$=Paw Withdrawal Threshold (g) at 1 hour after the administration of IB-MECA, gabapentin, amitriptyline, or combinations of IB-MECA with gabapentin or amitriptyline, and $PWT_{D7}$=Paw Withdrawal Threshold (grams) at D7 prior to drug administration. In the chemotherapeutic-induced neuropathic pain models, the % Prevention=($PWT_{IB-MECA}$-mean $PWT_{chemo}$)/(mean $PWT_{Veh}$-mean $PWT_{chemo}$)×100, where PWT=Paw Withdrawal Threshold, Chemo=paclitaxel or oxaliplatin and Veh=vehicle.

Statistical Analysis. Data are expressed as mean±SD for n animals. Behavioral data were analyzed by two-way repeated measures ANOVA with Bonferroni comparisons (full time course studies) or one-way ANOVA Dunnett's comparisons (1 hour behavioral data). The dose response curves were compared to a globally fitted curve using the extra sum-of-squares F-test comparisons to determine whether the data represented distinct curves between treatments. Significant differences were defined at a P<0.05. All statistical analysis was performed using GraphPad Prism (v5.03, GraphPad Software, Inc.).

Results $A_3AR$ agonists block the development of neuropathic pain following chronic constriction injury (CCI) via a mechanism believed to be mediated by $A_3AR$. When peak mechano-allodynia develops (at D7) following CCI of the mouse sciatic nerve [47], i.p. administration of IB-MECA, but not vehicle (0.1% DMSO in saline), rapidly (30 min) and dose-dependently (0.2-2 μmol/kg, n=5) reversed allodynia, with maximal effect within 1 hour ($ED_{50}$, 0.4 μmol/kg; 95% CI=0.23-0.66) (FIG. 1A). IB-MECA lacked effect on Paw Withdrawal Thresholds (PWT, grams) in contralateral paws (FIG. 1B). Noteworthy, when compared to D7, consecutive daily injections (0.5 μmol/kg IB-MECA, n=5) on D8-D15 reversed mechano-allodynia to the same degree as observed on D7 following the first injection (FIG. 1C). Without being bound to any particular theory, this suggests that $A_3ARs$ do not become tolerant to agonist activation, at least over this dosing paradigm.

Figure 2:
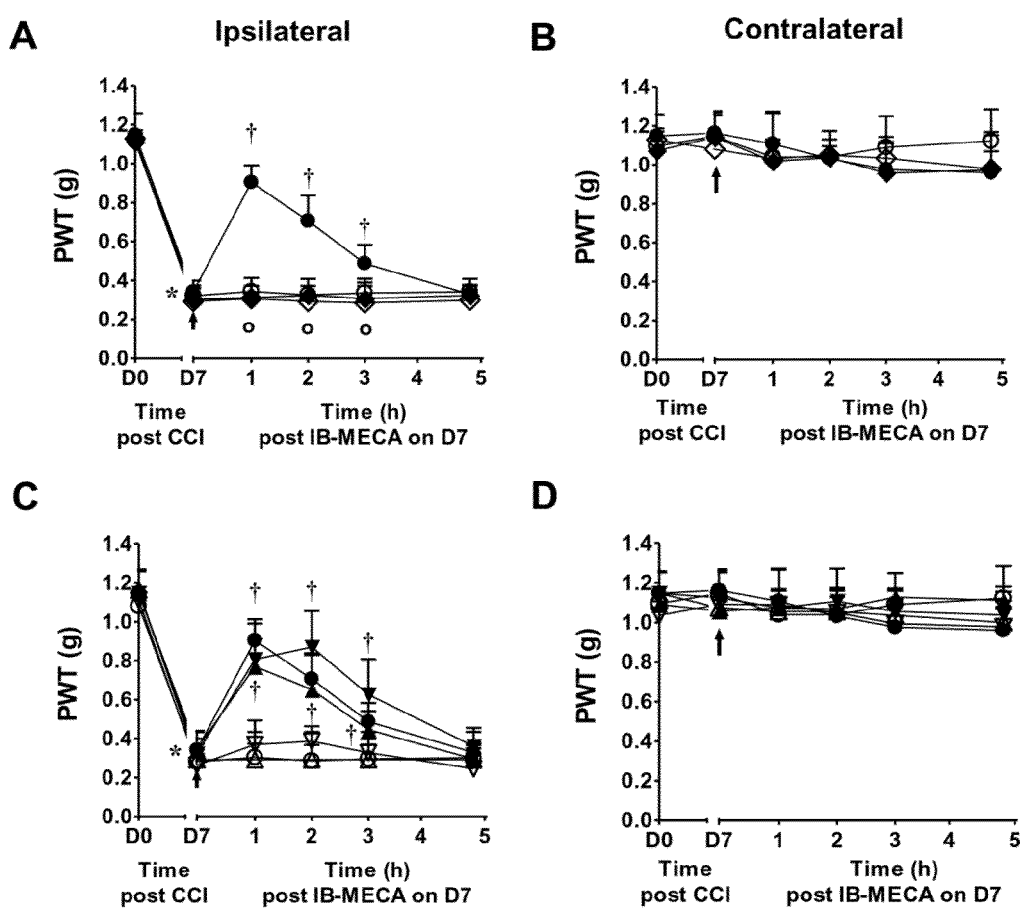
FIG. 2. IB-MECA reverses CCI-induced neuropathic pain through an apparently $A_3AR$-mediated mechanism(s). Mechano-allodynia developed by D7 after CCI of the sciatic nerve (○) in ipsilateral paws (A, C), but not contralateral paws (B, D), which was reversed by i.p. administration of IB-MECA (0.5 μmol/kg; ●; arrow). The $A_3AR$ antagonist, MRS1523 (i.p.; 5 μmol/kg; ◆; A), but not the $A_1AR$ antagonist, DPCPX (2 μmol/kg; ▲; C) or the $A_{2A}AR$ antagonist, SCH-442416 (i.p.; 0.2 μmol/kg; ▼; C) prevented the anti-allodynic effect of IB-MECA. Neither MRS1523 (◇), DPCPX (Δ) nor SCH-442416 (∇), when given alone, had any effect on allodynia on ipsilateral (A, C) or contralateral (B, D) paws. Antagonists were given 15 minutes before IB-MECA or its vehicle. Results are expressed as mean±SD for n=5 mice and analyzed by ANOVA with Bonferroni comparisons. *$P<0.001$ for D7 vs. D0; †$P<0.001$ for IB-MECA at $t_h$ vs. D7; and °$P<0.001$ for IB-MECA+antagonist vs. IB-MECA.

The anti-allodynic effect of IB-MECA (0.5 μmol/kg, n=5) was prevented by a 15 minutes pretreatment with a potent $A_3AR$ antagonist, MRS1523 (5 μmol/kg, n=5; FIG. 2A) [60]. MRS1523 is a 1,4-dihydropyridine derivative that binds to murine and rat $A_3ARs$ with high affinity and has moderate selectivity against $A_1AR$, but excellent selectivity against $A_{2A}AR$ and $A_2BAR$ (at least 1000-fold) [61]. In contrast, the anti-allodynic effect of IB-MECA (0.5 μmol/kg, n=5) was not affected by the potent $A_1AR$ antagonist, DPCPX (2 μmol/kg, n=5) or by the potent $A_{2A}AR$ antagonist, SCH-442416 (0.2 μmol/kg, n=5) (44) (FIG. 2C). When given alone on D7, MRS1523, DPCPX or SCH-442416 lacked effect on ipsilateral (FIG. 2A, C) or contralateral (FIG. 2B, D) PWT. Agonist and antagonist doses were chosen from previous studies showing selectivity for their respective receptor subtype [62-64].

Figure 3:
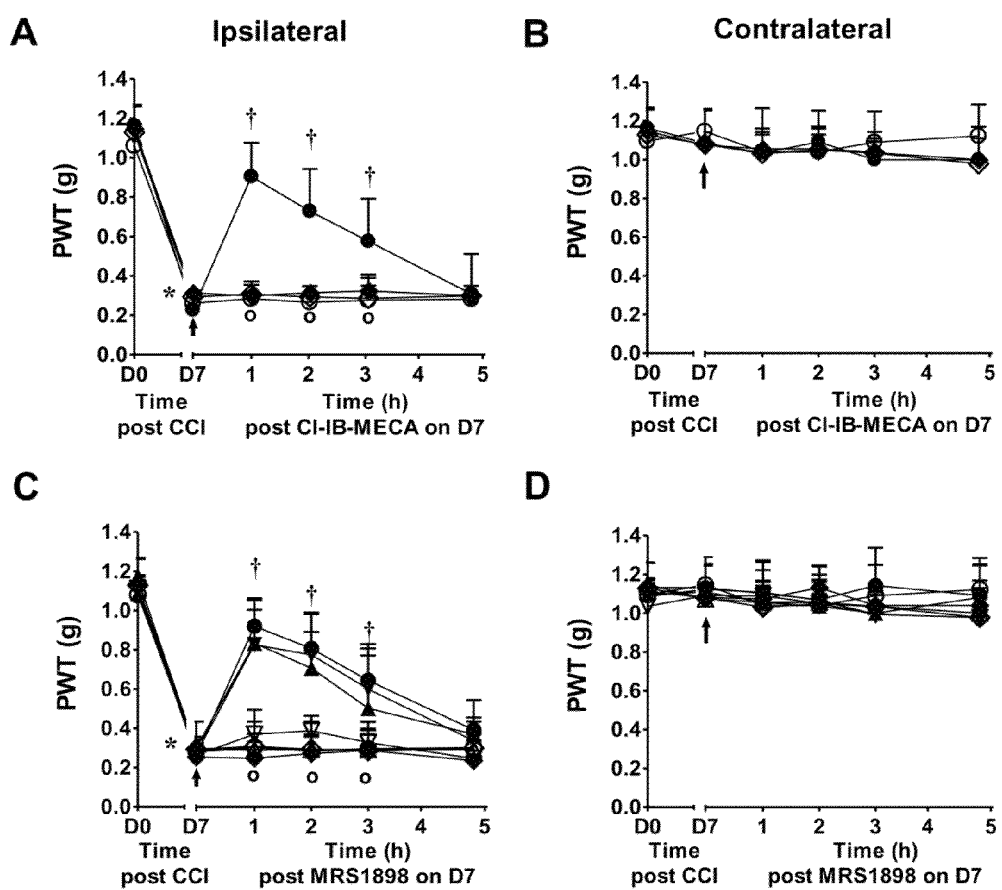
FIG. 3. CI-IB-MECA and MRS1898 reverse CCI-induced neuropathic pain through an apparently $A_3AR$-mediated mechanism. When given i.p. on D7 and compared to vehicle (○), administration (arrow) of CI-IB-MECA (0.6 μmol/kg; ●; A,B) or MRS1898 (0.5 μmol/kg; ●; C,D) reversed mechano-allodynia in ipsilateral (A, C), with no effects on contralateral paws (B, D). The $A_3AR$ antagonist, MRS1523 (5 μmol/kg; ◆), blocked the ability of CI-IB-MECA (A) or MRS1898 (C) to reverse mechano-allodynia. The $A_1AR$ antagonist, DPCPX (2 μmol/kg; ▲) or the $A_{2A}AR$ antagonist, SCH-442416 (i.p.; 0.2 μmol/kg; ▼) did not prevent the anti-allodynic effects of MRS1898 (C). Neither MRS1523 (◇), DPCPX (Δ) nor SCH-442416 (∇), when given alone, had any effect on allodynia on ipsilateral (A, C) or contralateral (B, D) paws. Antagonists were given 15 min before CI-IB-MECA and MRS1898 or its vehicle. Results are expressed as mean±SD for n=5 mice and analyzed by ANOVA with Bonferroni comparisons. *P<0.001 for D7 vs. D0; †P<0.001 for A$_3$AR agonists±antagonists at t$_h$ vs. D7; and °P<0.001 for A$_3$AR agonists+antagonist vs. agonists.

To prove that the benefit of $A_3AR$ agonists in neuropathic pain is independent of which $A_3AR$ agonist is used to treat the pain, two additional selective $A_3AR$ agonists were tested: Cl-IB-MECA, the 2-chlorinated analogue of IB-MECA, and the structurally distinct MRS1898. MRS1898 is a well-characterized, potent $A_3AR$ agonist containing a rigid bicyclic ring substitution of ribose that is believed to maintain a receptor-preferred conformation [45]. CI-IB-MECA (0.6 μmol/kg, n=5; FIG. 3A) and MRS1898 (0.5 μmol/kg, n=5; FIG. 3C) rapidly and maximally (≤1 h) reversed mechano-allodynia, effects blocked by MRS1523 (5 μmol/kg, n=5) (FIG. 3A) but not by DPCPX (2 μmol/kg, n=5) or SCH-442416 (0.2 μmol/kg, n=5) (FIG. 3C). Doses of CI-IB-MECA and MRS1898 were selected from previous studies [45]. CI-IB-MECA and MRS1898 had no effect on PWT in contralateral paws (FIG. 3B, D). Without being bound to any particular theory, such results indicate that $A_3AR$ agonists of two distinct classes reverse mechano-allodynia through an $A_3AR$-mediated mechanism and without involving other ARs.

Figure 4:
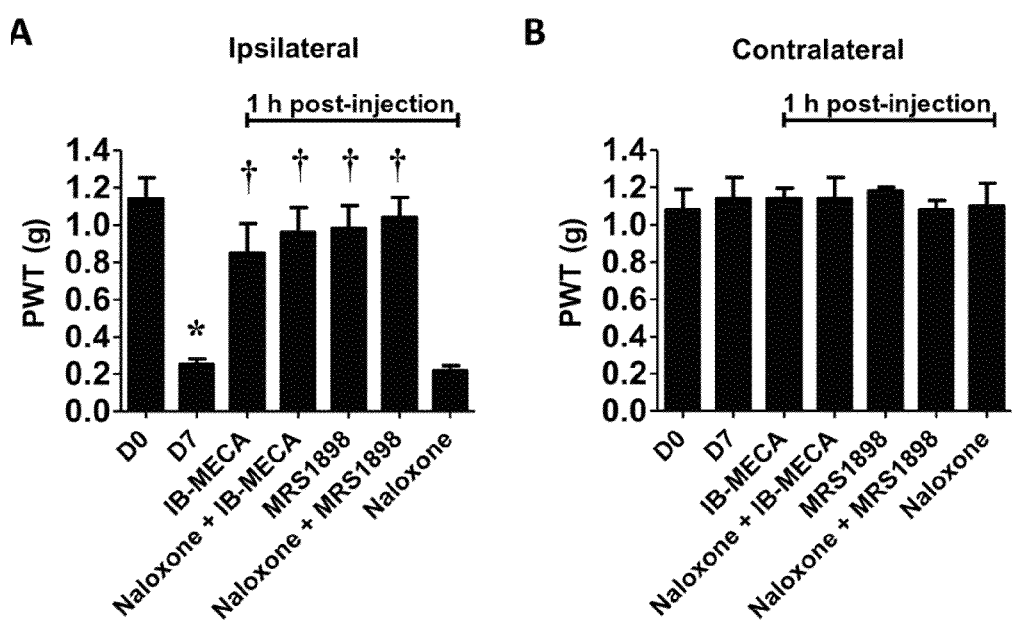
FIG. 4. Naloxone does not block anti-allodynic effects of A$_3$AR agonists. (A) In ipsilateral paws, the reversal of mechano-allodynia by IB-MECA or MRS1898 (0.5 µmol/kg) was not prevented by naloxone (25 µmol/kg). (B) No differences in PWT (grams) were observed in contralateral paws. Results are expressed as mean±SD, n=5 mice, analyzed by ANOVA with Dunnett's comparisons. *P<0.001 (D7 or vehicle vs. D0); †P<0.001 (IB-MECA at 1 hour post treatment vs. D7).

Anti-allodynic effects of $A_3AR$ agonists are naloxone-independent. A high dose (i.p.) of non-selective opioid receptor antagonist naloxone (25 μmol/kg, n=5) was administered 15 minutes before IB-MECA (0.5 μmol/kg, n=5) or MRS1898 (0.5 μmol/kg, n=5). Naloxone did not interfere with the ability of the $A_3AR$ agonists to reverse established mechano-allodynia in the CCI model (FIG. 4A), supporting the exclusion of an opioid-dependent mechanism. Given alone on D7, naloxone did not affect ipsilateral (FIG. 4A) or contralateral (FIG. 4B) PWT.

Figure 5:
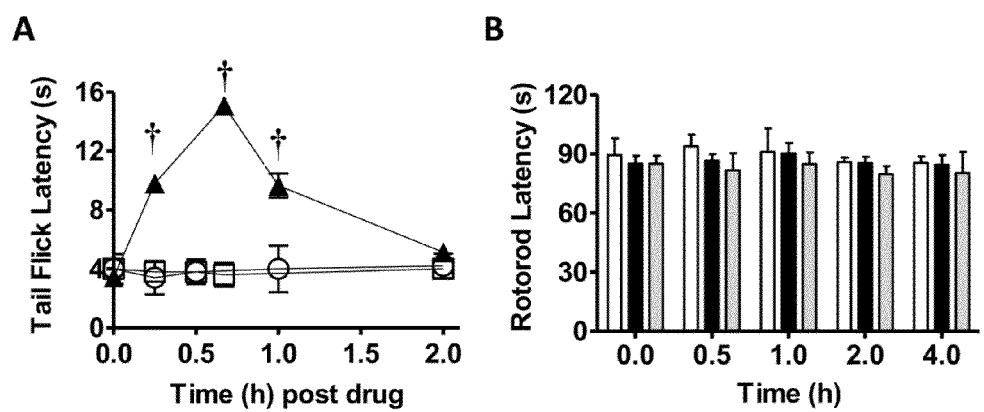
FIG. 5. A$_3$AR agonists have no effect on acute nociception and Rotarod test. (A) Unlike morphine (35 µmol/kg, s.c., ▲), IB-MECA (0.5 µmol/kg, ○) and MRS1898 (0.5 µmol/kg, □) lacked effect on mouse tail flick latency. (B) Mouse Rotarod Latency (s) was similar with IB-MECA (0.5 µmol/kg, black bar), MRS1898 (0.5 µmol/kg, grey bar) or vehicle (white bar). Results are expressed as mean±SD, n=5 mice, analyzed by ANOVA with Bonferroni comparisons. †P<0.001 (morphine vs. t$_{0h}$).

$A_3AR$ agonists have no effect on acute nociception. IB-MECA or MRS1898 (0.5 μmol/kg, n=5) tested at 30, 60 and 120 minutes lacked effect on acute nociception in the mouse tail flick (FIG. 5A). On the other hand, morphine injected s.c. (35 μmol/kg; n=5) and used as a positive control elicited potent acute antinociceptive effects with a significant (P<0.001) increase in tail flick latencies (FIG. 5A). Similarly, IB-MECA or MRS1898 (0.5 μmol/kg, n=5) had no effect when tested on the hot plate (not shown), supporting the lack of a role for $A_3AR$ agonists in modulating normal nociception.

$A_3AR$ agonists have no effect on the Rotarod test. IB-MECA or MRS1898 (0.5 μmol/kg, n=5) did not induce Rotarod deficits, thereby providing evidence countering potential motor function impairment in mice (FIG. 5B). In addition, $A_3AR$ agonists when tested at the highest dose lacked observable signs of lethargy or sedation i.e. the specimens exhibited normal posture, no loss of normal activity such as grooming, no effect on alert and exploratory behavior, no effect on spontaneous locomotor activity and no loss of motor coordination, paw dragging or their ability to remain upright.

Figure 6:
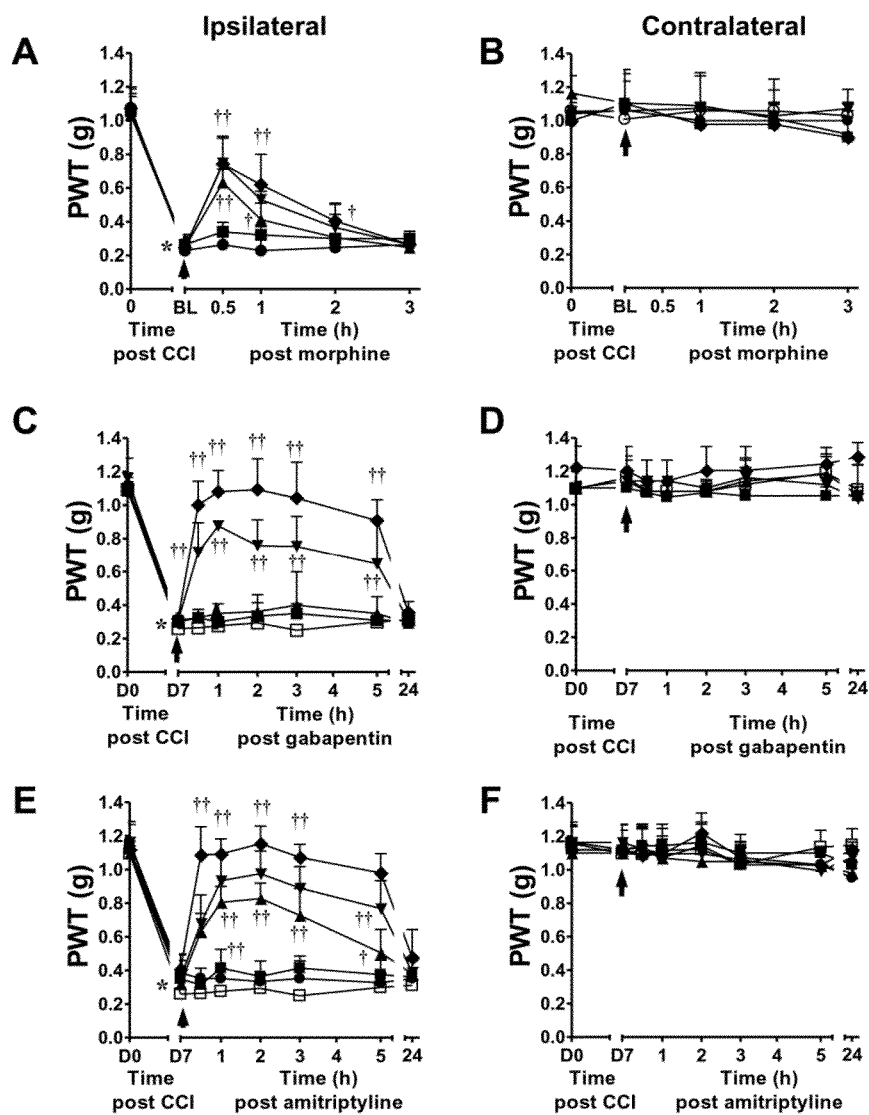
FIG. 6. Morphine, gabapentin, or amitriptyline reverse mechano-allodynia in CCI-induced neuropathic pain. The development of mechano-allodynia observed on D7 after CCI in the ipsilateral paw (□, n=6) was reversed in a dose and time-dependent manner by morphine (0.11, ○; 0.35, ●; 1.05, ■; 3.5, ▲; 11, ▼; or 35 µmol/kg, ♦; A), gabapentin (18, ■; 58, ▲; 175, ▼; or 584 µmol/kg, ♦; C) or amitriptyline (3.2, ○; 9.6, ■; 32, ▲; 96, ▼; or 191 µmol/kg, ♦; E) in ipsilateral paws. These agents had no effect in contralateral paws (B, D, F). Results are expressed as mean±SD for n=5 mice and analyzed by ANOVA with Bonferroni comparisons. *P<0.001 for D7 vs. D0; †P<0.05 or ††P<0.001 for morphine, gabapentin or amitriptyline at t$_h$ vs. D7.
Figure 7:
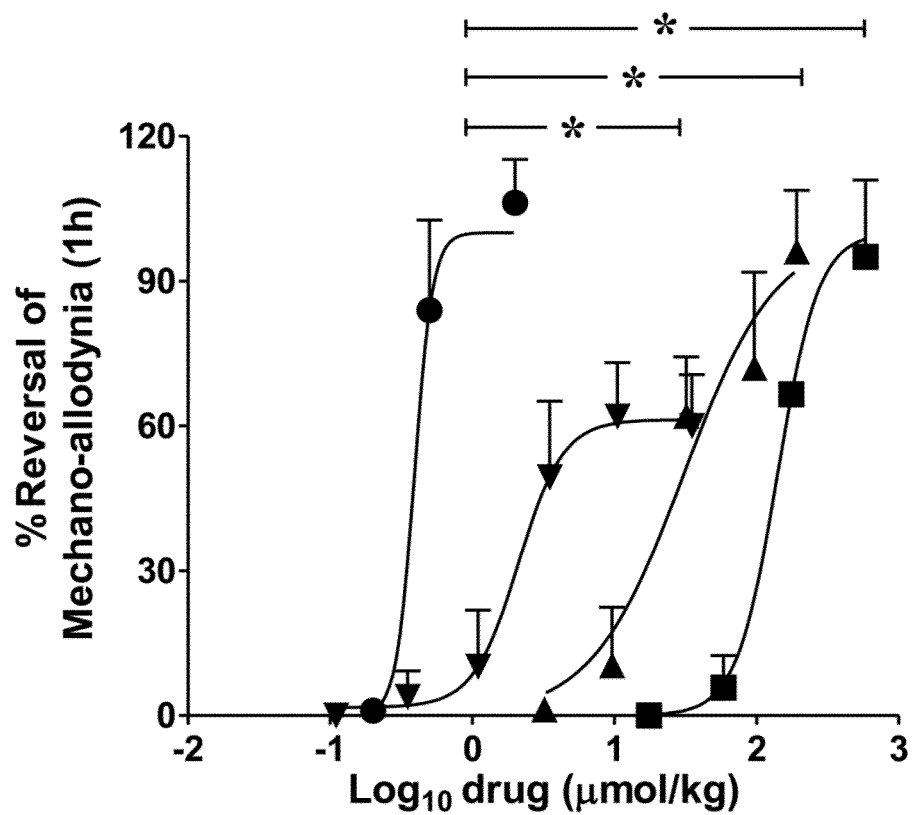
FIG. 7. Relative potencies of IB-MECA, morphine, gabapentin and amitriptyline in CCI. As tested on D7 and at time of peak reversal, IB-MECA was >5-, >350-, and >75-fold, respectively, more potent in reversing established mechano-allodynia when compared to morphine (▼), gabapentin (■) or amitriptyline (▲). In addition, IB-MECA was more efficacious than morphine but equiefficacious with gabapentin or amitriptyline. Results expressed as mean±SD, n=5 mice, difference between curves were analyzed by extra sum-of-squares F-test comparisons. *P<0.001 (morphine, gabapentin or amitriptyline vs. IB-MECA); †P<0.001 (morphine, gabapentin or amitriptyline vs. gabapentin, amitriptyline or morphine+IB-MECA).

IB-MECA increases the potency the analgesic effects of morphine, gabapentin and amitriptyline in CCI. Morphine (0.11-35 μmol/kg, n=5), but not its vehicle (saline), given s.c. on D7 led to a rapid peak 0.5 h) and dose-dependent reversal of mechano-allodynia in ipsilateral paws (FIG. 6A), but not in contralateral paws (FIG. 6B). Morphine at the time of maximal reversal (0.5 hours) displayed an $ED_{50}$ of 2.1 μmol/kg (95% CI=1.5-3.0), which was 5-fold less potent than IB-MECA (FIG. 7). Moreover, IB-MECA ($E_{max}$=100%) was more efficacious than morphine alone ($E_{max}$=62±3%, FIG. 7). Gabapentin (18-584 μmol/kg, i.p., n=5; FIG. 6C) or amitriptyline (3-191 μmol/kg, oral, n=5; FIG. 6E), but not their vehicle (saline), on D7 led to a rapid (≤0.5 h) and dose-dependent reversal of mechano-allodynia in ipsilateral paws that peaked at 1 hour. The $ED_{50}$ of gabapentin and amitriptyline at maximal reversal (1 hour) was, respectively, 140 μmol/kg (95% CI=122-162) and 31 μmol/kg (95% CI=22-43) (FIG. 7). Therefore, the gabapentin and amitriptyline were shown to be >350- and 75-fold less potent than IB-MECA. Gabapentin and amitriptyline had no effect on contralateral PWT (FIG. 6D, F).

Figure 8:
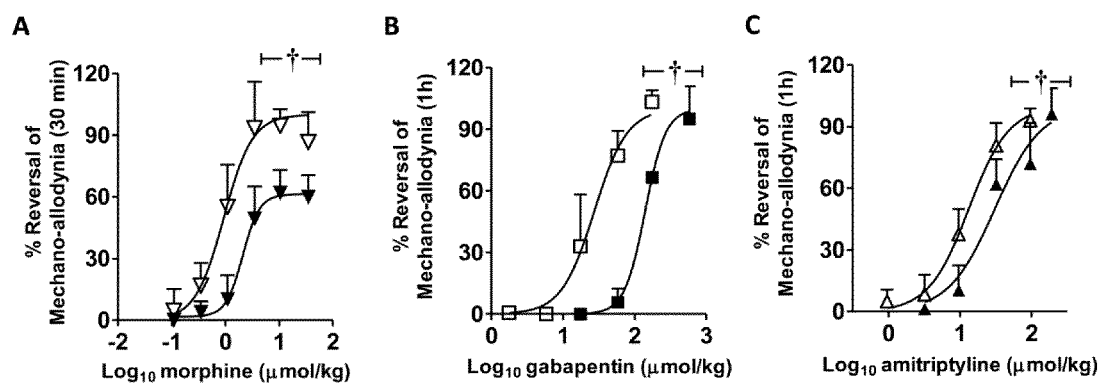
FIG. 8. IB-MECA augments the anti-allodynic effects of morphine, gabapentin or amitriptyline in CCI. When compared to morphine (0.11-35 µmol/kg, s.c., ▼, A), gabapentin (18-584 µmol/kg, i.p., ■, B) or amitriptyline (3-191 µmol/kg, oral, ▲, C) alone on D7, co-administration of a low dose of IB-MECA (0.2 µmol/kg) significantly increased their anti-allodynic effects as revealed by a shift to the left in the dose-response of morphine (∇, A), gabapentin (□, B) and amitriptyline (Δ, C). Moreover, IB-MECA (0.2 µmol/kg) increased the efficacy of morphine (A). Results expressed as mean±SD, n=5 mice, difference between curves were analyzed by extra sum-of-squares F-test comparisons. *P<0.001 (morphine, gabapentin or amitriptyline vs. IB-MECA); †P<0.001 (morphine, gabapentin or amitriptyline vs. gabapentin, amitriptyline or morphine+IB-MECA).

It is noteworthy that an IB-MECA dose devoid of anti-allodynic effects (0.2 μmol/kg, n=5) augmented the ability of morphine (0.11-35 μmol/kg, n=5; FIG. 8A), gabapentin (1.8-175 μmol/kg, n=5; FIG. 8B) or amitriptyline (1-96 μmol/kg, n=5; FIG. 8C) to reverse established mechano-allodynia, as evidenced by a significant (P<0.001) leftward dose response shift. To this end, the $ED_{50}$ at peak reversal for morphine decreased from 2.1 μmol/kg (95% CI=1.5-3.0) to 0.98 μmol/kg (95% CI=0.66-1.5) when combined with IB-MECA, whereas the $ED_{50}$ at peak reversal for gabapentin or amitriptyline decreased from 140 μmol/kg (95% CI=122-162) and 31 μmol/kg (95% CI=22-43) to 27 μmol/kg (95% CI=21-34) and 13 μmol/kg (95% CI=11-16) respectively when combined with IB-MECA. This combined treatment lacked effect on contralateral PWT (not shown). Collectively, IB-MECA increased the potency of morphine by >2-fold and that of gabapentin and amitriptyline by >5- and 2-fold, respectively. Moreover, IB-MECA also enhanced the efficacy of morphine by 1.6-fold (FIG. 8A).

$A_3AR$ agonists block the development of chemotherapy-induced neuropathic pain without interfering with antitumor effects. $A_3AR$ were tested in models of neuropathic pain induced by widely used chemotherapeutics in distinct classes and with well known, distinct antitumor mechanisms of action: paclitaxel, oxaliplatin and bortezomib. Although chemotherapeutic dosing in each model is completed within several days, $A_3AR$ agonists were administered until the time when pain typically occurs (usually between 15-17 days). When compared to vehicle, paclitaxel administration led to neuropathic pain (mechano-allodynia and mechano-hyperalgesia) that peaked by D16, plateaued through D25 and was dose-dependently attenuated by daily (D0-D15) administration of IB-MECA (0.02-0.2 μmol/kg/d, i.p., n=6; FIG. 9A, B) but not vehicle (0.1% DMSO in saline). The D16 $ED_{50}$ values for prevention of paclitaxel-induced mechano-allodynia and mechano-hyperalgesia were 0.02 and 0.03 μmol/kg/d (95% CI=0.018-0.024 and 0.024-0.033).

It is noteworthy that following discontinuation of IB-MECA treatment on D15, neuropathic pain did not emerge through D25 (FIG. 9A, B). The effects of IB-MECA (0.2 μmol/kg/d, n=6) were prevented by co-administration with MRS1523 (5 μmol/kg/d, n=6; FIG. 9C, D). Without being bound to any particular theory, this indicates that $A_3AR$ agonism is involved, since CI-IB-MECA (0.2 μmol/kg/d, n=5) or MRS1898 (0.2 μmol/kg/d, n=3) completely blocked paclitaxel-induced neuropathic pain (not shown) eliminating the possibility that a pharmacological action particular to IB-MECA causes the protective effects.

Figure 9:
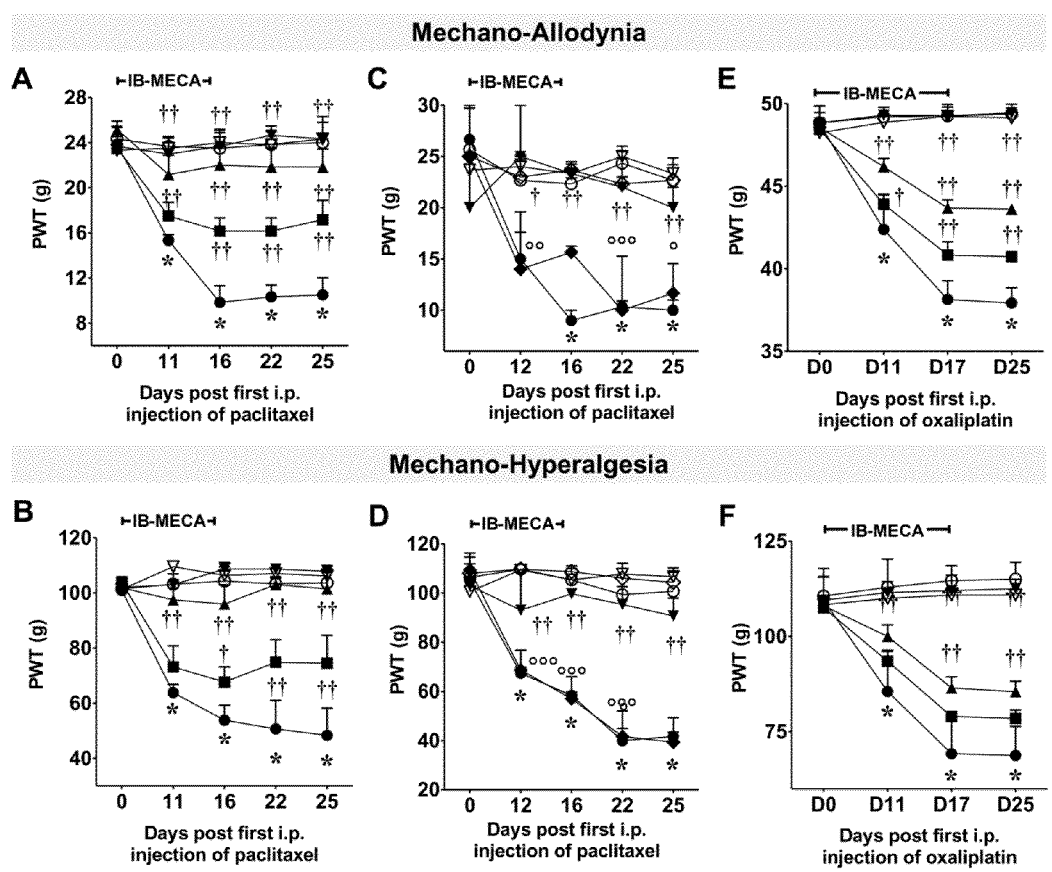
FIG. 9. IB-MECA blocks chemotherapy-induced neuropathic pain. When compared to the vehicle group (○), paclitaxel (●) or oxaliplatin (●) led to a time-dependent development of mechano-allodynia (A, E) and mechano-hyperalgesia (B, F), which was blocked by daily i.p. injections (D0-D15/D17) with IB-MECA (0.02, ■; 0.05, ▲; or 0.2 µmol/kg/d, ▼). Effects of IB-MECA (0.2 µmol/kg/d) in paclitaxel-induced neuropathic pain were antagonized by co-administration of MRS1523 (5 µmol/kg/d; ♦, C,D). At the highest dose, IB-MECA (0.2 µmol/kg, ∇, A-F) or MRS1523 (5 µmol/kg/d, ◊, C,D) alone lacked effect in vehicle groups. Results expressed as mean±SD, n=6 rats, analyzed by ANOVA with Bonferroni comparisons. *P<0.001 (chemotherapeutic agent vs. vehicle); †P<0.01 or ††P<0.001 (chemotherapeutic agent+IB-MECA vs. chemotherapeutic agent); and °P<0.05, °°P<0.01 or °°°P<0.001 (paclitaxel+IB-MECA+MRS1523 vs. paclitaxel+IB-MECA).

The beneficial effects of IB-MECA were not restricted to paclitaxel. Indeed, the development of oxaliplatin-induced neuropathic pain (peaking by D17 and plateauing through D25) was attenuated dose-dependently by daily (D0-D17) administration of IB-MECA (0.02-0.2 μmol/kg/d, n=6; FIG. 9E, F) and did not emerge upon drug termination. IB-MECA prevented mechano-allodynia and mechano-hyperalgesia with D17 with $ED_{50}$ values of 0.05 and 0.06 μmol/kg/d, respectively (95% CI=0.039-0.053 and 0.048-0.07). Finally, IB-MECA (0.2 μmol/kg/d, n=5) blocked the development of bortezomib-induced mechano-allodynia and mechano-hyperalgesia, which did not emerge when treatment was discontinued on D17 (not shown). IB-MECA administered alone (0.2 μmol/kg/d, n=6) did not affect PWT in any of the chemotherapy models used (FIG. 9).

Additional experiments confirming an $A_3AR$-dependent mechanism in oxaliplatin- or bortezomib-induced neuropathic pain were unnecessary as the IB-MECA doses matched those used with paclitaxel. None of the drugs tested affected body weight, and all animals gained weight to the same extent over the course of the experiment (not shown). The potent antitumor effects of $A_3AR$ agonists are well documented [65]. The effects of IB-MECA on the antitumor activity of paclitaxel in human breast cancer cells (SKBR3) [45], oxaliplatin in human colon cancer cells (SW480) [46], or bortezomib in human multiple myeloma cells (RPMI 8226) [57] were assessed using a MTT (3-(4,5-dimethylthiazol-2-yl)-2,5-diphenyltetrazolium bromide) assay adapted from a previously described assay [58, 59]. At a dose yielding <20% decrease in cell survival when used alone, IB-MECA (10 nM) did not diminish the antitumor effects of paclitaxel, oxaliplatin or bortezomib on human breast, colon and multiple myeloma cancer cells (Table 1, below). Higher doses of IB-MECA were not used, because these doses had direct antitumor effects on all three cell lines tested and so could interact positively with antitumor effects of the chemotherapeutic to provide benefit.

TABLE 1

| Treatment | $LD_{50}$ | n-value | P-value |
|---|---|---|---|
| SKBR3 breast cancer cells | | | |
| Paclitaxel | 7.0 nM | 5 | 1.0 |
| Paclitaxel + IB-MECA (10 nM) | 7.1 nM | 5 | |
| SW480 colon cancer cells | | | |
| Oxaliplatin | 3.8 µM | 6 | 0.89 |
| Oxaliplatin + IB-MECA (10 nM) | 3.2 µM | 6 | |
| RPMI 8226 multiple myeloma cells | | | |
| Bortezomib | 27 nM | 5 | 0.25 |
| Bortezomib + IB-MECA (10 nM) | 29 nM | 5 | |

REFERENCES

1. Fishman, P. & Bar-Yehuda, S. Pharmacology and therapeutic applications of A3 receptor subtype. Curr Top Med Chem 3, 463-469 (2003).
2. Jacobson, K. A. Adenosine A3 receptors: novel ligands and paradoxical effects. Trends Pharmacol Sci 19, 184-191 (1998).
3. Kim, H. O., et al. 2-Substitution of N6-benzyladenosine-5'-uronamides enhances selectivity for A3 adenosine receptors. J Med Chem 37, 3614-3621 (1994).
4. De Grandis, D. Acetyl-L-carnitine for the treatment of chemotherapy-induced peripheral neuropathy: a short review. CNS Drugs 21 Suppl 1, 39-43; discussion 45-36 (2007).
5. Cata, J. P., Weng, H. R., Lee, B. N., Reuben, J. M. & Dougherty, P. M. Clinical and experimental findings in humans and animals with chemotherapy-induced peripheral neuropathy. Minerva Anestesiol 72, 151-169 (2006).
6. Farquhar-Smith, P. Chemotherapy-induced neuropathic pain. Curr Opin Support Palliat Care 5, 1-7 (2011).
7. Polomano, R. C. & Bennett, G. J. Chemotherapy-evoked painful peripheral neuropathy. Pain Med 2, 8-14 (2001).
8. Dougherty, P. M., Cata, J. P., Cordella, J. V., Burton, A. & Weng, H. R. Taxol-induced sensory disturbance is characterized by preferential impairment of myelinated fiber function in cancer subjects. Pain 109, 132-142 (2004).
9. Lynch, J. J., 3rd, Wade, C. L., Zhong, C. M., Mikusa, J. P. & Honore, P. Attenuation of mechanical allodynia by clinically utilized drugs in a rat chemotherapy-induced neuropathic pain model. Pain 110, 56-63 (2004).
10. Polomano, R. C., Mannes, A. J., Clark, U. S. & Bennett, G. J. A painful peripheral neuropathy in the rat produced by the chemotherapeutic drug, paclitaxel. Pain 94, 293-304 (2001).
11. Fishman, P., Bar-Yehuda, S., Madi, L. & Cohn, I. A3 adenosine receptor as a target for cancer therapy. Anticancer Drugs 13, 437-443 (2002).
12. Flatters, S. J. & Bennett, G. J. Studies of peripheral sensory nerves in paclitaxel-induced painful peripheral neuropathy: evidence for mitochondrial dysfunction. Pain 122, 245-257 (2006).
13. Jin, H. W., Flatters, S. J., Xiao, W. H., Mulhern, H. L. & Bennett, G. J. Prevention of paclitaxel-evoked painful peripheral neuropathy by acetyl-L-carnitine: effects on axonal mitochondria, sensory nerve fiber terminal arbors, and cutaneous Langerhans cells. Exp Neurol 210, 229-237 (2008).
14. Bennett, G. J. & Xie, Y. K. A peripheral mononeuropathy in rat that produces disorders of pain sensation like those seen in man. Pain 33, 87-107 (1988).
15. Randall, L. O. & Selitto, J. J. A method for measurement of analgesic activity on inflamed tissue. Arch Int Pharmacodyn Ther 111, 409-419 (1957).
16. Dixon, W. J. Efficient analysis of experimental observations. Annu Rev Pharmacol Toxicol 20, 441-462 (1980).
17. Taliani, L., Pugliesi, I., Bellandi, M., La Motta, C. & Da Settimo, F. $A_3$ receptor ligands: past, present and future trends.
18. Göblyös, A. & Izjerman, P. Allosteric modulation of adenosine receptors.
19. Torrance, N., Smith, B. H., Bennett, M. I., and Lee, A. J. (2006) The epidemiology of chronic pain of predominantly neuropathic origin. Results from a general population survey. J Pain 7, 281-289.
20. Farquhar-Smith, P. (2011) Chemotherapy-induced neuropathic pain. Curr Opin Support Palliat Care 5, 1-7.
21. Cata, J. P., Weng, H. R., Lee, B. N., Reuben, J. M., and Dougherty, P. M. (2006) Clinical and experimental findings in humans and animals with chemotherapy-induced peripheral neuropathy. Minerva Anestesiol 72, 151-169.
22. Finnerup, N. B., Sindrup, S. H., and Jensen, T. S. (2010) The evidence for pharmacological treatment of neuropathic pain. Pain 150, 573-581.
23. Fredholm, B. B., AP, I. J., Jacobson, K. A., Linden, J., and Muller, C. E. (2011) International Union of Basic and Clinical Pharmacology. LXXXI. Nomenclature and classification of adenosine receptors—an update. Pharmacol Rev 63, 1-34.
24. Fredholm, B. B., AP, I. J., Jacobson, K. A., Klotz, K. N., and Linden, J. (2001) International Union of Pharmacology. XXV. Nomenclature and classification of adenosine receptors. Pharmacol Rev 53, 527-552.
25. Kumar, V., and Sharma, A. (2009) Adenosine: an endogenous modulator of innate immune system with therapeutic potential. Eur J Pharmacol 616, 7-15.
26. Fishman, P., and Bar-Yehuda, S. (2003) Pharmacology and therapeutic applications of A3 receptor subtype. Curr Top Med Chem 3, 463-469.
27. Fishman, P., Bar-Yehuda, S., Madi, L., and Cohn, I. (2002) A3 adenosine receptor as a target for cancer therapy. Anticancer Drugs 13, 437-443.
28. Kiesman, W. F., Elzein, E., and Zablocki, J. (2009) A1 adenosine receptor antagonists, agonists, and allosteric enhancers. Handb Exp Pharmacol, 25-58.

29. Taliani, S., Pugliesi, I., Bellandi, M., La Motta, C., and Da Settimo, F. (2010) A3 receptor ligands: past, present and future trends. Curr Top Med Chem 10, 942-975.
30. Zylka, M. J. (2011) Pain-relieving prospects for adenosine receptors and ectonucleotidases. Trends Mol Med 17, 188-196.
31. Loram, L. C., Harrison, J. A., Sloane, E. M., Hutchinson, M. R., Sholar, P., Taylor, F. R., Berkelhammer, D., Coats, B. D., Poole, S., Milligan, E. D., Maier, S. F., Rieger, J., and Watkins, L. R. (2009) Enduring Reversal of Neuropathic Pain by a Single Intrathecal Injection of Adenosine 2A Receptor Agonists: A Novel Therapy for Neuropathic Pain. J Neurosci 29, 14015-14025.
32. Jacobson, K. A., Gao, Z. G., Goblyos, A., and Ijzerman, A. P. (2011) Allosteric modulation of purine and pyrimidine receptors. Adv Pharmacol 61, 187-220.
33. Jacobson, K. A. (1998) Adenosine A3 receptors: novel ligands and paradoxical effects. Trends Pharmacol Sci 19, 184-191.
34. Kim, H. O., Ji, X. D., Siddiqi, S. M., Olah, M. E., Stiles, G. L., and Jacobson, K. A. (1994) 2-Substitution of N6-benzyladenosine-5'-uronamides enhances selectivity for A3 adenosine receptors. J Med Chem 37, 3614-3621.
35. Silverman, M. H., Strand, V., Markovits, D., Nahir, M., Reitblat, T., Molad, Y., Rosner, I., Rozenbaum, M., Mader, R., Adawi, M., Caspi, D., Tishler, M., Langevitz, P., Rubinow, A., Friedman, J., Green, L., Tanay, A., Ochaion, A., Cohen, S., Kerns, W. D., Cohn, I., Fishman-Furman, S., Farbstein, M., Yehuda, S. B., and Fishman, P. (2008) Clinical evidence for utilization of the A3 adenosine receptor as a target to treat rheumatoid arthritis: data from a phase II clinical trial. J Rheumatol 35, 41-48.
36. Poulsen, S. A., and Quinn, R. J. (1998) Adenosine receptors: new opportunities for future drugs. Bioorg Med Chem 6, 619-641.
37. Ochaion, A., Bar-Yehuda, S., Cohen, S., Barer, F., Patoka, R., Amital, H., Reitblat, T., Reitblat, A., Ophir, J., Konfino, I., Chowers, Y., Ben-Horin, S., and Fishman, P. (2009) The anti-inflammatory target A3 adenosine receptor is overexpressed in rheumatoid arthritis, psoriasis and Crohn's disease. Cell Immunol 258, 115-122.
38. Abbracchio, M. P., Rainaldi, G., Giammarioli, A. M., Ceruti, S., Brambilla, R., Cattabeni, F., Barbieri, D., Franceschi, C., Jacobson, K. A., and Malorni, W. (1997) The A3 adenosine receptor mediates cell spreading, reorganization of actin cytoskeleton, and distribution of Bcl-XL: studies in human astroglioma cells. Biochem Biophys Res Commun 241, 297-304.
39. Ru, F., Surdenikova, L., Brozmanova, M., and Kollarik, M. (2011) Adenosine-induced activation of esophageal nociceptors. Am J Physiol Gastrointest Liver Physiol 300, G485-493.
40. Zhang, M., Hu, H., Zhang, X., Lu, W., Lim, J., Eysteinsson, T., Jacobson, K. A., Laties, A. M., and Mitchell, C. H. (2010) The A3 adenosine receptor attenuates the calcium rise triggered by NMDA receptors in retinal ganglion cells. Neurochemistry international 56, 35-41.
41. Lopes, L. V., Rebola, N., Pinheiro, P. C., Richardson, P. J., Oliveira, C. R., and Cunha, R. A. (2003) Adenosine A3 receptors are located in neurons of the rat hippocampus. Neuroreport 14, 1645-1648.
42. Jacobson, K. A., Nikodijevic, O., Shi, D., Gallo-Rodriguez, C., Olah, M. E., Stiles, G. L., and Daly, J. W. (1993) A role for central A3-adenosine receptors. Mediation of behavioral depressant effects. FEBS Lett 336, 57-60.
43. Giannaccini, G., Betti, L., Palego, L., Fabbrini, L., Schmid, L., Castagna, M., Giusti, L., Mascia, G., and Lucacchini, A. (2008) Species comparison of adenosine receptor subtypes in brain and testis. Neurochem Res 33, 852-860.
44. Yoon, M. H., Bae, H. B., and Choi, J. I. (2005) Antinociception of intrathecal adenosine receptor subtype agonists in rat formalin test. Anesth Analg 101, 1417-1421.
45. Tchilibon, S., Joshi, B. V., Kim, S. K., Duong, H. T., Gao, Z. G., and Jacobson, K. A. (2005) (N)-methanocarba 2,N6-disubstituted adenine nucleosides as highly potent and selective A3 adenosine receptor agonists. J Med Chem 48, 1745-1758.
46. Gao, Z. G., Teng, B., Wu, H., Joshi, B. V., Griffiths, G. L., and Jacobson, K. A. (2009) Synthesis and pharmacological characterization of [125I]MRS1898, a high-affinity, selective radioligand for the rat A3 adenosine receptor. Purinergic Signal 5, 31-37.
47. Bennett, G. J., and Xie, Y. K. (1988) A peripheral mononeuropathy in rat that produces disorders of pain sensation like those seen in man. Pain 33, 87-107.
48. Polomano, R. C., Mannes, A. J., Clark, U. S., and Bennett, G. J. (2001) A painful peripheral neuropathy in the rat produced by the chemotherapeutic drug, paclitaxel. Pain 94, 293-304.
49. Zheng, H., Xiao, W. H., and Bennett, G. J. (2011) Functional deficits in peripheral nerve mitochondria in rats with paclitaxel- and oxaliplatin-evoked painful peripheral neuropathy. Exp Neurol 232(2):154-61.
50. Dixon, W. J. (1980) Efficient analysis of experimental observations. Annu Rev Pharmacol Toxicol 20, 441-462.
51. Randall, L. O., and Selitto, J. J. (1957) A method for measurement of analgesic activity on inflamed tissue. Arch Int Pharmacodyn Ther 111, 409-419.
52. D'Amour, F. (1941) A method for determining loss of pain sensation. J Pharmacol xp Ther 72, 74-79.
53. Ndengele, M. M., Cuzzocrea, S., Masini, E., Vinci, M. C., Esposito, E., Muscoli, C., Petrusca, D. N., Mollace, V., Mazzon, E., Li, D., Petrache, I., Matuschak, G. M., and Salvemini, D. (2009) Spinal ceramide modulates the development of morphine antinociceptive tolerance via peroxynitrite-mediated nitroxidative stress and neuroimmune activation. J Pharmacol Exp Ther 329, 64-75.
54. Wang, Z. Q., Porreca, F., Cuzzocrea, S., Galen, K., Lightfoot, R., Masini, E., Muscoli, C., Mollace, V., Ndengele, M., Ischiropoulos, H., and Salvemini, D. (2004) A newly identified role for superoxide in inflammatory pain. J Pharmacol Exp Ther 309, 869-878.
55. Yi, D., Smythe, G. A., Blount, B. C., and Duncan, M. W. (1997) Peroxynitrite-mediated nitration of peptides: characterization of the products by electrospray and combined gas chromatography-mass spectrometry. Arch Biochem Biophys 344, 253-259.
56. Dahan, L., Sadok, A., Formento, J. L., Seitz, J. F., and Kovacic, H. (2009) Modulation of cellular redox state underlies antagonism between oxaliplatin and cetuximab in human colorectal cancer cell lines. Br J Pharmacol 158, 610-620.
57. Pellat-Deceunynk, C., Amiot, M., Bataille, R., Van Riet, I., Van Camp, B., Omede, P., and Boccadoro, M. (1995) Human myeloma cell lines as a tool for studying the biology of multiple myeloma: a reappraisal 18 years after [letter]. Blood 86, 4001-4002.
58. Shah, M. R., Kriedt, C. L., Lents, N. H., Hoyer, M. K., Jamaluddin, N., Klein, C., and Baldassare, J. (2009) Direct intra-tumoral injection of zinc-acetate halts tumor growth in a xenograft model of prostate cancer. J Exp Clin Cancer Res 28, 84.

59. Kriedt, C. L., Baldassare, J., Shah, M., and Klein, C. (2010) Zinc functions as a cytotoxic agent for prostate cancer cells independent of culture and growth conditions. J Exp Ther Oncol 8, 287-295.
60. Li, A. H., Moro, S., Melman, N., Ji, X. D., and Jacobson, K. A. (1998) Structure-activity relationships and molecular modeling of 3,5-diacyl-2,4-dialkylpyridine derivatives as selective A3 adenosine receptor antagonists. J Med Chem 41, 3186-3201.
61. Kreckler, L. M., Wan, T. C., Ge, Z. D., and Auchampach, J. A. (2006) Adenosine inhibits tumor necrosis factor-alpha release from mouse peritoneal macrophages via A2A and A2B but not the A3 adenosine receptor. J Pharmacol Exp Ther 317, 172-180.
62. Zheng, J., Wang, R., Zambraski, E., Wu, D., Jacobson, K. A., and Liang, B. T. (2007) Protective roles of adenosine A1, A2A, and A3 receptors in skeletal muscle ischemia and reperfusion injury. Am J Physiol Heart Circ Physiol 293, H3685-3691.
63. Cohen, S., Stemmer, S., Zozulya, G., Ochaion, A., Patoka, R., Barer, F., Bar-Yehuda, S., Rath-Wolfson, L., Jacobson, K., and Fishman, P. (2010) CF102 an $A_3$ adenosine receptor agonist mediates anti-tumor and anti-inflammatory effects in the liver. J Cell Physiol, 226, 2438-2447.
64. Ge, Z. D., Peart, J. N., Kreckler, L. M., Wan, T. C., Jacobson, M. A., Gross, G. J., and Auchampach, J. A. (2006) CI-IB-MECA [2-chloro-N6-(3-iodobenzyl)adenosine-5'-N-methylcarboxamide] reduces ischemia/reperfusion injury in mice by activating the A3 adenosine receptor. J Pharmacol Exp Ther 319, 1200-1210.
65. Fishman, P., Bar-Yehuda, S., Liang, B. T., and Jacobson, K. A. (2012) Pharmacological and therapeutic effects of $A_3$ adenosine receptor agonists. Drug Discov Today, in press.
66. Foley, K. M. (1995) Misconceptions and controversies regarding the use of opioids in cancer pain. Anticancer Drugs 6 Suppl 3, 4-13.
67. Joseph, E. K., and Levine, J. D. (2004) Caspase signalling in neuropathic and inflammatory pain in the rat. Eur J Neurosci 20, 2896-2902.
68. Watkins, L. R., Milligan, E. D., and Maier, S. F. (2001) Glial activation: a driving force for pathological pain. Trends Neurosci 24, 450-455.
69. Bennett, G. J. (2010) Pathophysiology and animal models of cancer-related painful peripheral neuropathy. Oncologist 15 Suppl 2, 9-12.
70. Shen, H., Chen, G. J., Harvey, B. K., Bickford, P. C., and Wang, Y. (2005) Inosine reduces ischemic brain injury in rats. Stroke 36, 654-659.
71. Von Lubitz, D. K., Lin, R. C., Boyd, M., Bischofberger, N., and Jacobson, K. A. (1999) Chronic administration of adenosine A3 receptor agonist and cerebral ischemia: neuronal and glial effects. Eur J Pharmacol 367, 157-163.
72. Fedorova, I. M., Jacobson, M. A., Basile, A., and Jacobson, K. A. (2003) Behavioral characterization of mice lacking the A3 adenosine receptor: sensitivity to hypoxic neurodegeneration. Cell Mol Neurobiol 23, 431-447.
73. Chen, G. J., Harvey, B. K., Shen, H., Chou, J., Victor, A., and Wang, Y. (2006) Activation of adenosine A3 receptors reduces ischemic brain injury in rodents. J Neurosci Res 84, 1848-1855.
74. Hentschel, S., Lewerenz, A., and Nieber, K. (2003) Activation of A3 receptors by endogenous adenosine inhibits synaptic transmission during hypoxia in rat cortical neurons. Restor Neurol Neurosci 21, 55-63.
75. Wunderlich, J. E., Needleman, B. J., Chen, Z., Yu, J. G., Wang, Y., Grants, I., Mikami, D. J., Melvin, W. S., Cooke, H. J., and Christofi, F. L. (2008) Dual purinergic synaptic transmission in the human enteric nervous system. Am J Physiol Gastrointest Liver Physiol 294, G554-566.
76. Rubaj, A., Zgodzinski, W., and Sieklucka-Dziuba, M. (2003) The influence of adenosine A3 receptor agonist: IB-MECA, on scopolamine- and MK-801-induced memory impairment. Behav Brain Res 141, 11-17.
77. Tchilibon, S., et al. (2005) (N)-methanocarba 2, $N^6$-disubstituted adenine nucleosides as highly potent and selective $A_3$ adenosine receptor antagonists. J. Med. Chem. 48, 1745-1758.
78. Kim, H. O., et al. (1994) Substitution of $N^6$-benzyladenosine-5'-uronamides enhances selectivity for $A_3$ adenosine receptors. J. Med. Chem. 37, 3614-3621 (1994).
79. Gao, Z. G., et al. (2009) Synthesis and pharmacological characterization of [($^{125}$)I]MRS 1898, a high-affinity, selective radioligand for the rat A(3) adenosine receptor. Purinegic Signal 5, 31-37.
80. Ge, Z. D., et al. (2006) CI-IB-MECA [2-Chloro-$N^6$-(3-iodobenzyl)adenosine-5'-N-methylcarboxamide] reduces ischemia/reperfusion injury in mice by activating the $A_3$ adenosine receptor. J Pharmacol Exp Ther 319, 1200-1210 (2006).
81. Tosh, D. K. et al. (2009) Functionalized congeners of $A_3$ adenosine receptor-selective nucleosides containing a bicycle[3.1.0]hexane ring system. J Med Chem 52, 7580-7592.
82. Tosh, D. K., et al. (2010) 2-Dialkynyl derivatives of (N)-methanocarba nucleosides: "clickable" $A_3$ adenosine receptor-selective agonist. Bioorg Med Chem 18, 508-517.
83. Chanyshev, B., et al. (2012) Anti-ischemic effects of multivalent dendrimeric $A_3$ adenosine receptor agonists in cultured cardiomyocytes and in the isolated rat heart. Pharmacol Res 65, 338-346.
84. Wan, T. C. et al. (2011) Polyamidoamine (PAMAM) dendrimer conjugate specifically activates the $A_3$ adenosine receptor to improve post-ischemic/reperfusion function in isolated mouse hearts. BMC Pharmacol 11, 11.

I claim:

1. A method of treating a mammalian subject experiencing neuropathic pain, comprising administering to the subject a pharmaceutical composition comprising a therapeutically effective amount of an $A_3AR$ agonist selected from the group consisting of: $N^6$-(3-iodobenzyl)-adenosine-5'-N-methyluronamide; 2-chloro-$N^6$-(3-iodobenzyl)-adenosine-5'-N-methyluronamide; (1R,2R,3S,4R)-4-(2-chloro-6-((3-chlorobenzyl)amino)-9H-purin-9-yl)-2,3-di-hydroxy-N-methylbicyclo[3.1.0]hexane-1-carboxamide; (2S,3S,4R,5R)-3-amino-5-[6-(2,5-dichlorobenzylamino)purin-9-yl]-4-hydroxytetrahydrofuran-2-carboxylic acid methylamide; (1'S,2'R,3'S,4'R,5'S)-4-(2-chloro-6-(3-chlorobenzylamino)-9H-purin-9-yl)-2,3-dihydroxy-N-methylbicyclo[3.1.0]hexane-1-carboxamide; 2-(1-hexynyl)-$N^6$-methyladenosine); (1S,2R,3S,4R)-2,3-dihydroxy-4-(6-((3-iodobenzyl)amino)-4H-purin-9 (5H)-yl)-N-methylcyclopentanecarboxamide); (1S,2R,3S,4R)-4-(2-chloro-6-((3-iodobenzyl)amino)-4H-purin-9 (5H)-yl)-2,3-dihydroxy-N-)methylcyclopentanecarboxamide; 2-cyclohexyl-N-(3,4-dichlorophenyl)-1H-imidazo[4,5-c]quinolin-4-amine; (1'R,2'R,3'S,4'R,5'S)-4-{2-chloro-6-[(3-iodophenylmethyl)amino]purin-9-yl-}-1-(methylaminocarbonyl)-bicyclo[3.1.0]hexane-2,3-diol, and combinations thereof.

2. The method of claim 1, wherein the $A_3AR$ agonist is $N^6$-(3-iodobenzyl)-adenosine-5'-N-methyluronamide.

3. The method of claim 1, wherein the neuropathic pain is due to a cause selected from the group consisting of spinal cord injury, multiple sclerosis, stroke, diabetes, herpes zoster infection, HIV-related neuropathies, nutritional deficiencies, toxins, remote manifestations of malignancies, immune mediated disorders, physical trauma to a nerve trunk, cancer, chemotherapy, radiation injury, surgery, and combinations thereof.

4. The method of claim 1, wherein the neuropathic pain is due to chemotherapy.

5. The method of claim 4, wherein the pain is due to the administration to the subject of a chemotherapeutic agent selected from the group consisting of podophyllotoxins, taxanes, platinum complexes, vinca alkaloids, proteasome inhibitors, colchicines, eribulin, lenolidamide, ixabepilone, interferons, thalidomide, etoposide, ifosfamide, procarbazine, cytarabine, gemcitabine, arsenic, and combinations thereof.

6. The method of claim 4, wherein the neuropathic pain is due to the administration of paclitaxel to the subject.

7. The method of claim 1, wherein the mammalian subject is a human.

8. A method of treating a mammalian subject experiencing neuropathic pain, comprising administering to the subject a first amount of an $A_3AR$ agonist and a second amount of an analgesic, wherein the first and second amounts together comprise a therapeutically effective amount, wherein the $A_3AR$ agonist is selected from the group consisting of: $N^6$-(3-iodobenzyl)-adenosine-5'-N-methyluronamide; 2-chloro-$N^6$-(3-iodobenzyl)-adenosine-5'-N-methyluronamide; (1R,2R,3S,4R)-4-(2-chloro-6-((3-chlorobenzyl)amino)-9H-purin-9-yl)-2,3-di-hydroxy-N-methylbicyclo[3.1.0]hexane-1-carboxamide; (2S,3S,4R,5R)-3-amino-5-[6-(2,5-dichlorobenzylamino)purin-9-yl]-4-hydroxytetrahydrofuran-2-carboxylic acid methylamide; (1'S,2'R,3'S,4'R,5'S)-4-(2-chloro-6-(3-chlorobenzylamino)-9H-purin-9-yl)-2,3-dihydroxy-N-methylbicyclo[3.1.0]hexane-1-carboxamide; 2-(1-hexynyl$N^6$-methyladenosine); (1S,2R,3S,4R)-2,3-dihydroxy-4-(6-((3-iodobenzyl)amino)-4H-purin-9 (5H)-yl)-N-methylcyclopentanecarboxamide); (1S,2R,3S,4R)-4-(2-chloro-6-((3-iodobenzyl)amino)-4H-purin-9 (5H)-yl)-2,3-dihydroxy-N-)methylcyclopentanecarboxamide; 2-cyclohexyl-N-(3,4-dichlorophenyl)-1H-imidazo[4,5-c]quinolin-4-amine; (1'R,2'R,3'S,4'R,5'S)-4-{2-chloro-6-[(3-iodophenylmethyl)amino]purin-9-yl-}-1-(methylaminocarbonyl)-bicyclo[3.1.0]hexane-2,3-diol, and combinations thereof.

9. The method of claim 8, wherein the analgesic is selected from the group consisting of opioids, morphinomimetics, antidepressants, antiepileptic, NMDA receptor antagonists, fatty acid amine hydrolyase inhibitors, anticonvulsants, antidepressants, non-steroidal anti-inflammatory drugs, calcium channel subunit $\alpha_2\delta$ ligands, COX-2 inhibitors, NOS inhibitors, and combinations thereof.

10. The method of claim 8, wherein the analgesic is selected from the group consisting of an opioid, a tricyclic antidepressant, a calcium channel subunit $\alpha_2\delta$ ligand, and combinations thereof.

11. The method of claim 8, wherein the analgesic is selected from the group consisting of morphine, gabapentin, pregabalin, amitriptyline, and combinations thereof.

12. The method of claim 8, wherein the neuropathic pain is induced due to a cause selected from the group consisting of spinal cord injury, multiple sclerosis, stroke, diabetes, herpes zoster infection, HIV-related neuropathies, nutritional deficiencies, toxins, remote manifestations of malignancies, immune mediated disorders, physical trauma to a nerve trunk, cancer, chemotherapy, radiation injury, surgery, and combinations thereof.

13. The method of claim 8, wherein the mammalian subject is a human.

14. The method of claim 8, wherein the neuropathic pain is due to chemotherapy.

15. The method of claim 14, wherein the pain is due to the administration to the subject of a chemotherapeutic agent selected from the group consisting of podophyllotoxins, taxanes, platinum complexes, vinca alkaloids, proteasome inhibitors, colchicines, eribulin, lenolidamide, ixabepilone, interferons, thalidomide, etoposide, ifosfamide, procarbazine, cytarabine, gemcitabine, arsenic, and combinations thereof.

16. The method of claim 14, wherein the neuropathic pain is due to the administration of paclitaxel to the subject.

17. The method of claim 8, wherein the $A_3AR$ agonist is $N^6$-(3-iodobenzyl)-adenosine-5'-N-methyluronamide.

18. A pharmaceutical composition comprising a first amount of an $A_3AR$ agonist and a second amount of an analgesic, wherein the first and second amounts taken together comprise a pharmaceutically effective amount and are dispersed are in a pharmaceutically acceptable carrier, wherein the $A_3AR$ agonist is selected from the group consisting of: $N^6$-(3-iodobenzyl)-adenosine-5'-N-methyluronamide; 2-chloro-$N^6$-(3-iodobenzyl)-adenosine-5'-N-methyluronamide; (1R,2R,3S,4R)-4-(2-chloro-6-((3-chlorobenzyl)amino)-9H-purin-9-yl)-2,3-di-hydroxy-N-methylbicyclo[3.1.0]hexane-1-carboxamide; (2S,3S,4R,5R)-3-amino-5-[6-(2,5-dichlorobenzylamino)purin-9-yl]-4-hydroxytetrahydrofuran-2-carboxylic acid methylamide; (1'S,2'R,3'S,4'R,5'S)-4-(2-chloro-6-(3-chlorobenzylamino)-9H-purin-9-yl)-2,3-dihydroxy-N-methylbicyclo[3.1.0]hexane-1-carboxamide; 2-(1-hexynyl)$N^6$-methyladenosine; (1S,2R,3S,4R)-2,3-dihydroxy-4-(6-((3-iodobenzyl)amino)-4H-purin-9(5H)-yl)-N-methylcyclopentanecarboxamide); (1S,2R,3S,4R)-4-(2-chloro-6-((3-iodobenzyl)amino)-4H-purin-9(5H)-yl)-2,3-dihydroxy-N-methylcyclopentanecarboxamide; 2-cyclohexyl-N-(3,4-dichlorophenyl)-1H-imidazo[4,5-c]quinolin-4-amine; (1'R,2'R,3'S,4'R,5'S)-4-{2-chloro-6-[(3-iodophenylmethyl)amino]purin-9-yl-}-1-(methylaminocarbonyl)-bicyclo[3.1.0]hexane-2,3-diol, and combinations thereof.

19. The pharmaceutical composition of claim 18, wherein the analgesic is selected from the group consisting of opioids, morphinomimetics, antidepressants, antiepileptic, NMDA receptor antagonists, fatty acid amine hydrolyase inhibitors, anticonvulsants, antidepressants, non-steroidal anti-inflammatory drugs, calcium channel subunit $\alpha_2\delta$ ligands, COX-2 inhibitors, NOS inhibitors, and combinations thereof.

20. The pharmaceutical composition of claim 18, wherein the analgesic is selected from the group consisting of morphine, gabapentin, pregabalin, amitriptyline, and combinations thereof.

* * * * *

UNITED STATES PATENT AND TRADEMARK OFFICE
CERTIFICATE OF CORRECTION

| | | |
|---|---|---|
| PATENT NO. | : 9,132,131 B2 | |
| APPLICATION NO. | : 13/420111 | |
| DATED | : September 15, 2015 | |
| INVENTOR(S) | : Daniela Salvemini | |

It is certified that error appears in the above-identified patent and that said Letters Patent is hereby corrected as shown below:

In the Claims:

In claim 1, column 24, lines 56-57, delete "N-)methylcyclopentanecarboxamide" and insert --N-methylcyclopentanecarboxamide-- therefor.

In claim 8, column 25, line 34, delete "hexynyl$N^6$" and insert --hexynyl)$N^6$-- therefor.

In claim 8, column 25, line 34, delete "methyladenosine)" and insert --methyladenosine-- therefor.

In claim 8, column 25, line 36, delete "methylcyclopentanecarboxamide)" and insert --methylcyclopentanecarboxamide-- therefor.

In claim 8, column 25, line 38, delete "dihydroxy-N-)" and insert --dihydroxy-N- -- therefor.

Signed and Sealed this
Twenty-third Day of August, 2016

Michelle K. Lee
*Director of the United States Patent and Trademark Office*